US008548786B2

(12) United States Patent
Plenz

(10) Patent No.: US 8,548,786 B2
(45) Date of Patent: Oct. 1, 2013

(54) NEURONAL AVALANCHE ASSAY

(75) Inventor: Dietmar Plenz, Chevy Chase, MD (US)

(73) Assignee: The United States of America, as represented by the Secretary, Department of Health & Human Services, Washington, DC (US)

(*) Notice: Subject to any disclaimer, the term of this patent is extended or adjusted under 35 U.S.C. 154(b) by 1513 days.

(21) Appl. No.: 11/990,419

(22) PCT Filed: Aug. 14, 2006

(86) PCT No.: PCT/US2006/031884
§ 371 (c)(1),
(2), (4) Date: Feb. 12, 2008

(87) PCT Pub. No.: WO2007/022208
PCT Pub. Date: Feb. 22, 2007

(65) Prior Publication Data
US 2009/0036791 A1 Feb. 5, 2009

Related U.S. Application Data

(60) Provisional application No. 60/707,651, filed on Aug. 12, 2005.

(51) Int. Cl.
*G06G 7/58* (2006.01)
*G01N 33/48* (2006.01)
*G01N 33/50* (2006.01)
*G01N 31/00* (2006.01)
*G06F 19/00* (2011.01)

(52) U.S. Cl.
CPC ..................................... *G06F 19/34* (2013.01)
USPC .................... 703/11; 703/12; 702/19; 702/22

(58) Field of Classification Search
None
See application file for complete search history.

(56) References Cited

U.S. PATENT DOCUMENTS

| 5,331,970 | A | * | 7/1994 | Gevins et al. | 600/544 |
|---|---|---|---|---|---|
| 5,792,186 | A | | 8/1998 | Rise | |
| 6,029,157 | A | | 2/2000 | Mihatsch | |
| 6,297,025 | B1 | | 10/2001 | Sugihara et al. | |
| 6,434,419 | B1 | | 8/2002 | Gevins et al. | |
| 6,511,817 | B1 | | 1/2003 | Lynch et al. | |
| 7,299,089 | B2 | | 11/2007 | Wolf et al. | |
| 2004/0137515 | A1 | | 7/2004 | Lynch et al. | |

(Continued)

FOREIGN PATENT DOCUMENTS

| EP | 1 590 665 | 6/2006 |
|---|---|---|
| EP | 1 192 461 | 4/2007 |
| WO | WO 2004/023983 | 3/2004 |

OTHER PUBLICATIONS

Beggs JM, Plenz D, Neuronal Avalanches in Neocortical Circuits, *The Journal of Neuroscience*, 23(35): 11167-77 (2003).

(Continued)

*Primary Examiner* — Russell S Negin
(74) *Attorney, Agent, or Firm* — Edwards Wildman Palmer LLP; Peter F. Corless; Christine C. O'Day

(57) ABSTRACT

Method and system for determining a cognitive enhancement and/or anti-epileptic effect comprising: detecting synchronized neuronal activity in neuronal tissue (601), monitoring spreading of the synchronized neuronal activity (602), determining a parameter (604, 605) indicative of the closeness of the synchronized neuronal activity to the critical state and comparing (613) the parameter to a predetermined value.

27 Claims, 26 Drawing Sheets

(56) References Cited

U.S. PATENT DOCUMENTS

2006/0212089 A1 9/2006 Tass
2007/0043402 A1 2/2007 Echauz et al.
2007/0067003 A1 3/2007 Sanchez et al.

OTHER PUBLICATIONS

Beggs JM, Plenz D, Neuronal Avalanches Are Diverse and Precise Activity Patterns That Are Stable for Many Hours in Cortical Slice Cultures, *The Journal of Neuroscience*, 24(22): 5216-29 (2004).

Dharmaraj et al., Neuronal Avalanches in the Human EEG, Draft Manuscript dated Dec. 6, 2007.

Hahn et al., Neuronal Avalanches In Vivo and In Spiking Activity, presented at the 37th annual meeting of the Society for Neuroscience, Nov. 3-7, 2007 in San Diego, CA (poster No. 637.9/EEE6).

Hauptmann et al., Intermittent Burst Synchronization in Neural Networks, in the 7th International Work-Conference on Artificial and Natural Neural Networks, IWANN 2003, Maó, Menorca, Spain, Jun. 3-6. Proceedings, Part I, Series: Lecture Notes in Computer Science, 2686: 46-53 (2003).

Petermann et al., The Supercritical Working Brain, presented at the 37th annual meeting of the Society for Neuroscience, Nov. 3-7, 2007 in San Diego, CA (poster No. 637.9/EEE6).

Thiagarajan et al., A Novel Form of Metastability in Cortex, presented at the 37th annual meeting of the Society for Neuroscience, Nov. 3-7, 2007 in San Diego, CA (poster No. 761.1).

Gireesh E et al., Neuronal avalanches organize as nested theta-and beta/gamma-oscillations during development of cortical layer 2/3. PNAS May 27, 2008;105(21): 7576-7581.

Stewart CV, Plenz D. "Homeostatis of neuronal avalanches during postnatal cortex development in vitro." J. Neurosci Methods, 2007, doi:10.1016/j.jneumeth.2007.10.021.

Plenz, Comment on "Critical Branching Captures Activity in Living Neural Networks and Maximizes the Number of Metastable States." Phys. Rev. Lett. 2005, 95: 219801, published on Nov. 14, 2005.

Hobbs, "Aberrant Neuronal Avalanches in Cortical Tissue Removed From Juvenile Epilepsy Patients." J. Clin. Neurophys. 2010, 27(6): 380-386.

Plenz, "Neuronal avalanches and coherence potentials." The European Physical Journal Special Topics 205(1): 259-301, published in 2012.

* cited by examiner

A SCH23390 (D1R antagonist)

a₁ Control, SCH23390, Wash

B Sulpiride (D2R antagonist)

b₁ Control, Sulpiride, Wash

NEURONAL AVALANCHE ASSAY

CROSS REFERENCE TO RELATED PATENT APPLICATIONS

This application is the national stage entry of PCT/US2006/031884 filed Aug. 14, 2006, which claims priority to U.S. Provisional Application No. 60/707,651 filed Aug. 12, 2005, both of which are herein incorporated by reference in their entirety.

BACKGROUND OF THE INVENTION

Transient formation of synchrony might serve as an integrative mechanism to bind neurons into coherent cell assemblies that are fundamental to cortical function. Such synchronization has been observed during visual stimulus discrimination, cognitive categorization tasks, potential motor command signals, and is similar to internally generated synchrony. However, understanding of the dynamical processes that underlie such fast and selective synchronization has been largely limited to computational models rather than biological networks. In these models, stable and spatially selective propagation of synchrony without distortion, decay or explosion can only occur when key parameters are set in a narrow range, particularly when synchronization emerges locally within large networks. These difficulties persist even when the constraints on synchronization are lowered to the propagation of transient firing rate increases, calling into question the ability of biological cortical networks to stably propagate synchrony.

There is a need for methods and systems for analyzing properties of propagation within 'neuronal avalanches' and utilizing the ability of cortical networks to support the propagation of precise patterns of synchrony within multiple cortical areas and across multiple cortical columns.

SUMMARY OF THE INVENTION

Provided are systems and methods for determining a cognitive enhancement and/or anti-epileptic effect comprising detecting synchronized neuronal activity in neuronal tissue, monitoring spreading of the synchronized neuronal activity, determining a parameter indicative of the closeness of the synchronized neuronal activity to the critical state, and comparing the parameter to a predetermined value.

Further provided are systems and methods for determining a cognitive enhancement and/or anti-epileptic effect comprising detecting synchronized neuronal activity in neuronal tissue, monitoring spreading of the synchronized neuronal activity, determining a slope of a size distribution of the synchronized neuronal activity, comparing the slope of the size distribution to a threshold slope, determining a ratio of successively propagated synchronized neuronal activity, and comparing the ratio to a threshold ratio.

Still further provided are systems and methods for screening compositions for a cognitive enhancement and/or anti-epileptic effect comprising applying a composition to neuronal tissue, measuring propagated synchronized activity in the neuronal tissue, determining a parameter indicative of the closeness of the synchronized neuronal activity to the critical state, and comparing the parameter to a predetermined value.

Additional advantages of the invention will be set forth in part in the description which follows or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 2 C is a raster plot of nLFP activity.

FIGS. 2 D and E illustrate avalanche size distributions.

DETAILED DESCRIPTION OF THE INVENTION

Figure 1:
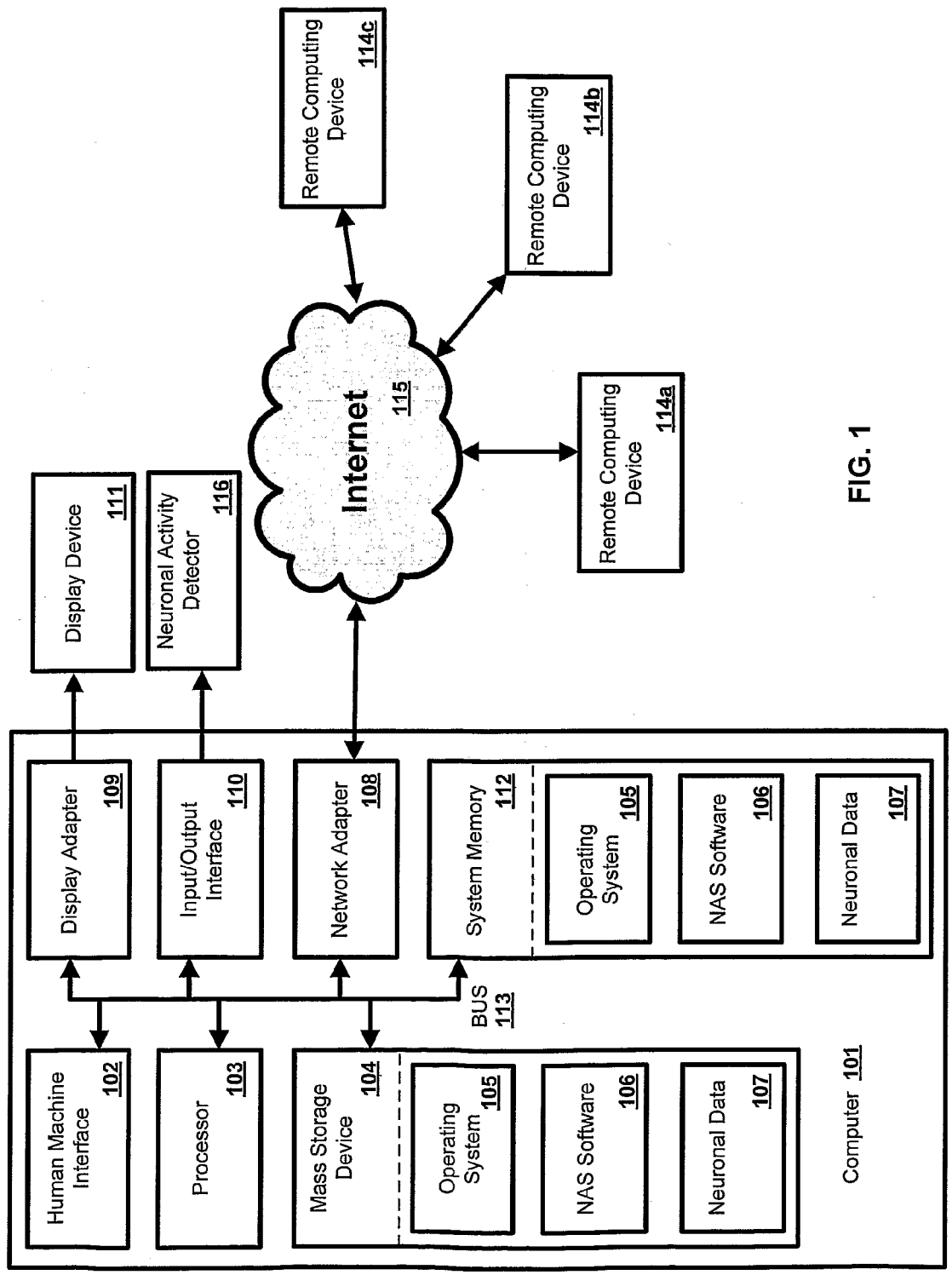
FIG. 1 illustrates an exemplary operating environment.

Before the present methods and systems are disclosed and described, it is to be understood that this invention is not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

The present invention may be understood more readily by reference to the following detailed description of preferred embodiments of the invention and the Examples included therein and to the Figures and their previous and following description.

Provided herein in are methods and systems for performing a Neuronal Avalanche Assay (NAS-assay). The NAS-assay uses the spatial distribution of synchronized activity, in neuronal tissue. For exemplary purposes, the description is directed toward the NAS-assay using local field potentials (LFP). In the LFP, the activity of a single neuron is barely detectable, however, if many neurons synchronize their activities, the LFP is large enough to be registered by a local recording device, in this case, the microelectrode. As LFPs propagate along an array of microelectrodes, the neuronal activity can be analyzed for neuronal avalanches.

However, any method with which synchronized neuronal activity can be detected locally in the living brain and which allows for the monitoring of the spread of synchronized activity, can be used in the NAS-assay. The NAS-assay, in its principle design, is not limited to the use of LFPs only.

An example is the measurement of local synchronized activity using Magentoencephalography (MEG). In the MEG, the tiny magnetic currents induced by a single neuron are not detectable, however, if many neurons synchronize their activities, the change in the magnetic field is measurable with high spatial (~1 mm) and temporal resolution (~1 ms). MEG is therefore very similar to the LFP measurements in monitoring the spread of synchronized neuronal activity in living tissue.

The NAS assay can be constructed from common forms of synchronized activities, by way of example and not limitation, coherent delta/theta-(2-8 Hz) and gamma-(>25 Hz) oscillations measured from superficial cortical layers. Such oscillations are readily revealed in Electroencephalogram (EEG) measurements. This allows the use of an EEG as a neuronal activity detector for the NAS-assay.

The NAS-assay can utilize MEG, EEG, and the like. Any technique that allows for the monitoring of the propagation of synchronized neuronal activities with high spatial (~1 mm) and temporal (~1 ms) resolution can be used.

I. EXEMPLARY SYSTEM

One skilled in the art will appreciate that what follows is a functional description and that the respective functions can be performed by software, hardware, or a combination of software and hardware.

FIG. 1 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The systems and methods of the present invention can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

In another aspect, the systems and methods of the present invention can be described in the general context of computer instructions, such as program modules, being executed by a computer. Generally, program modules comprise routines, programs, objects, components, data structures, etc. that perform particular tasks or implement particular abstract data types. The systems and methods of the present invention can also be practiced in distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 101. The components of the computer 101 can comprise, but are not limited to, one or more processors or processing units 103, a system memory 112, and a system bus 113 that couples various system components including the processor 103 to the system memory 112.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (USA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus also known as a Mezzanine bus. The bus 113, and all buses specified in this description can also be implemented over a wired or wireless network connection and each of the subsystems, including the processor 103, a mass storage device 104, an operating system 105, NAS software 106, neuronal data 107, a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computer 101 typically comprises a variety of computer readable media. Exemplary readable media can be any available media that is accessible by the computer 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as neuronal data 107 and/or program modules such as operating system 105 and NAS software 106 that are immediately accessible to and/or are presently operated on by the processing unit 103.

In another aspect, the computer 101 can also comprise other removable/non-removable, volatile/non-volatile computer storage media. By way of example, FIG. 1 illustrates a mass storage device 104 which can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and NAS software 106. Each of the operating system 105 and NAS software 106 (or some combination thereof) can comprise elements of the programming and the NAS software 106. Neuronal data 107 can also be stored on the mass storage device 104. Neuronal data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 101 via an input device (not shown). Examples of such input devices comprise, but are not limited to, a keyboard, pointing device (e.g., a "mouse"), a microphone, a joystick, a scanner, and the like. These and other input devices can be connected to the processing unit 103 via a human machine interface 102 that is coupled to the system bus 113, but can be, connected by other interface and bus structures, such as a parallel port, game port, an IEEE 1394 Port (also known as a Firewire port), a serial port, or a universal serial bus (USB).

In yet another aspect of the present invention, a display device 111 can also be connected to the system bus 113 via an interface, such as a display adapter 109. It is contemplated that the computer 101 can have more than one display adapter 109 and the computer 101 can have more than one display device 111. For example, a display device can be a monitor, an LCD (Liquid Crystal Display), or a projector. In addition to the display device 111, other output peripheral devices can comprise components such as speakers (not shown) and a printer (not shown) which can be connected to the computer 101 via Input/Output Interface 110.

A neuronal activity detector 116 can communicate with computer 101 via Input/Output Interface 110 or across a local or remote network. In one aspect, users utilize a neuronal activity detector that is capable of collecting neuronal data. It will be appreciated that the neuronal activity detector 116 can be any type of neuronal activity detector, for example and not meant to be limiting, a microelectrode array (to record LFPs and single/multi-unit activity), a surface electrode system (to record the EEG), a charge-coupled device camera (CCD) or photodiode array (to record activity-dependent fluorescence changes), a magnetometer type SQUID (superconducting quantum interference device) sensor (to record the MEG), and the like. In another aspect, the neuronal activity detector 116 can be an independent stand alone device, or can be integrated into another device. Optionally, the communication with computer 101 via Input/Output Interface 110 can be via a wired or wireless connection.

The computer 101 can operate in, a networked environment using logical connections to one or more remote computing devices 114a,b,c. By way of example, a remote computing device can be a personal computer, portable computer, a server, a router, a network computer, a peer device or other common network node, and so on. Logical connections between the computer 101 and a remote computing device 114a,b,c can be made via a local area network (LAN) and a general wide area network (WAN). Such network connections can be through a network adapter 108. A network adapter 108 can be implemented in both wired and wireless environments. Such networking environments are conventional and commonplace in offices, enterprise-wide computer networks, intranets, and the Internet 115.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of NAS software 106 can be stored on or transmitted across some form of computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The processing of the disclosed systems and methods of the present invention can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

The NAS Software 106 allows for the study of neuronal avalanches and includes many analysis features. NAS Software 106 allows for the calculation of alpha ($\alpha$), the slope of the avalanche size distribution, and sigma ($\sigma$), the branching parameter at the correct temporal resolution ($\Delta t_{avg}$). Avalanche calculation controls set the parameters for concatenating LFPs into avalanches. A multi-function control window contains functions that extract the avalanche parameters $\alpha$ and $\sigma$ at corresponding $\Delta t_{avg}$. For visual control, avalanche size distributions in log-log coordinates can be generated and displayed. Cross-correlation plots used to calculate $\Delta t_{avg}$ can also be displayed at various temporal resolutions. Additional features relate to the identification and labeling of recording locations to superficial cortical layers in which avalanches occur. For example, the NAS Software 106 allows for the topological identification of electrode positions on a microelectrode array with respect to brain region and cortical layer. NAS Software 106 allows for the storage of spatial information, e.g. images, and miscellaneous data specific to an experimental configuration.

NAS Software 106 can analyze the similarity in spatiotemporal organization between neuronal avalanches. The spatiotemporal organization of avalanche is highly diverse and the diversity can be used to further evaluate the quality of the data and to quantify the critical state in the cortical network. More specifically, the size distribution of significant avalanche families reveals a heavy-tail in family sizes that forms a power law with slope gamma ($\gamma$). Shuffle and cluster controls allow for the generation of shuffled data sets and statistical evaluation of family significance and calculation of $\gamma$. Several additional features allow for a detailed examination of avalanche similarity on which the family size distribution is based. An avalanche generation tree can be generated that represents the generational relationship between avalanches based on similarity. An avalanche similarity matrix can be generated that contains the similarity index for all possible pair wise comparisons between avalanches. A multi-function control window for cluster analysis contains functions for studying the spatiotemporal organization of avalanches, for example, displaying a family frequency distribution plot to derive $\gamma$.

NAS Software 106 allows for a detailed pair-wise comparison between individual avalanches selected from the similarity matrix. The spatiotemporal pattern of an avalanche can be indicated by a specific color representing active electrodes on successive 8×8 matrices for two avalanches simultaneously in order to study similarity features in further detail between two neuronal avalanches.

NAS Software 106 allows for visualization and editing of the temporal organization of neuronal avalanches. This can play a role when judging the quality of recorded data. An overview plot of LFP activity can be generated that displays the occurrence of LFPs during an experiment. A zoom view can display LFP occurrence for the temporal duration indicated by a colored rectangle in an overview plot. This allows for a detailed examination of avalanches and can be used to clean data sets from spurious noise. It also allows for the indication of avalanche extent and precise labeling of individual avalanches within a data set with respect to rank of occurrence in time, corresponding family and order within a family. For evoked activity, this feature can display identified stimuli and corresponding evoked avalanches. Family controls can display the type and occurrence of families over time. The family control and avalanche zoom view can be aligned in time for precise comparison.

II. EXEMPLARY METHODS

The methods will be described herein as applied to the use of a planar microelectrode array as a neuronal activity detector. Spontaneous neuronal activity can be studied with planar microelectrode arrays that contain, for example, 60-electrodes arranged on an 8×8 matrix at an interelectrode distance of 200 μm (30 μm electrode diameter; corner electrodes missing), and oriented such that cortical layers are in parallel with electrode rows.

A. Data Acquisition

Figure 2:
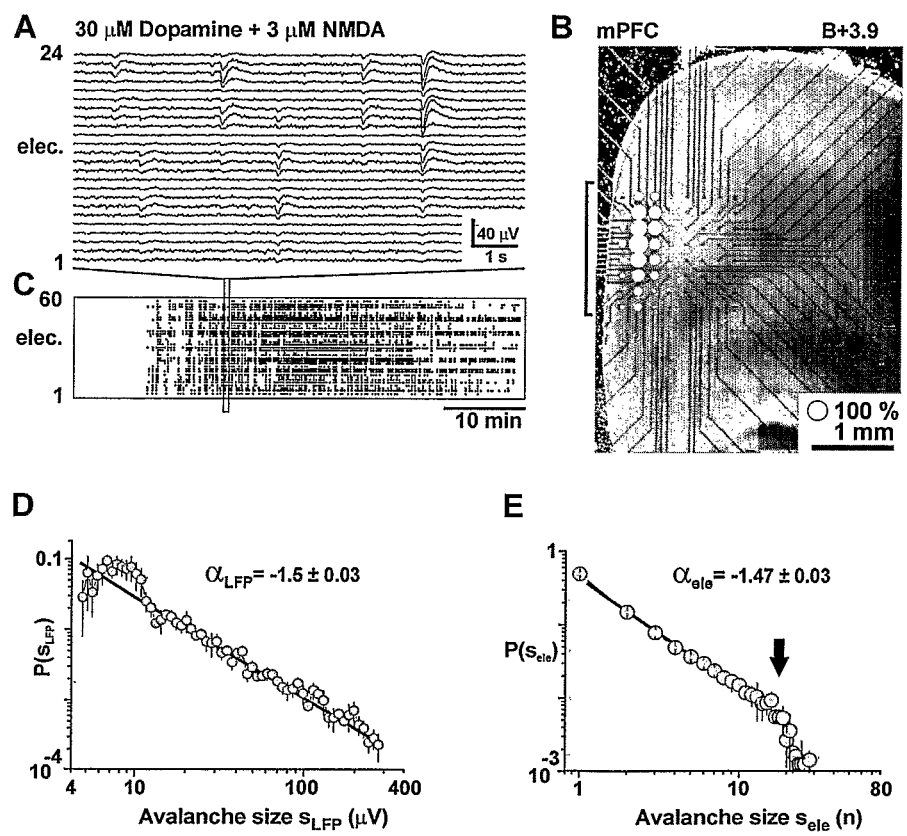
FIGS. 2 A and B show an example of continuous extracellular signals recorded with a microelectrode array in an acute brain slice from rat medial prefrontal cortex.

Continuous extracellular signals v(t) can be recorded between 0.1 Hz and 3000 Hz, low-pass filtered at 200 Hz (Butterfly-filter, Multichannel Systems), digitised at a rate of 1 kHz ($\Delta t$=1 ms) and stored. For each electrode k (k=[1, $n_{elec}$], $n_{elec}$=60), the electrode noise of v(t) can be estimated by calculating the mean and standard deviation (SD) of v(t) from the total duration of the recording, $T_{tot}$, which can range, for example, between 40-60 min. FIG. 2A,B shows an example of continuous extracellular signals recorded with a microelectrode array in an acute brain slice from rat medial prefrontal cortex. Negative LFP peaks (nLFPs) at electrode k can be detected by negative threshold crossing at −3 SD of electrode noise and can be characterized by the time and absolute amplitude of the negative LFP peak, $A^k(t_i)$, before v(t) returned to threshold. More precisely, at a given temporal resolution $\Delta t$, nLFPs at electrode k can be represented by a vector of length $n_{max}$, where $n_{max}$ is an integer value for which $T_{tot}=n_{max}\cdot\Delta t$. This vector can contain zeros, except for positions $t_i=i\cdot\Delta t$, i∈[1, . . . , $n_{max}$] with values $A^k(t_i)$ in μV. The resulting raster plot of nLFP activity is shown as an example in FIG. 2C.

B. Definition of Neuronal Avalanches

A neuronal avalanche is a sequence of consecutive time bins of width $\Delta t$ with at least one nLFP, which is preceded and terminated by at least one time bin with no activity (FIG. 3A). The absence of activity for a period of $\Delta t$ thus indicates the end of an avalanche. If the decision of whether an avalanche has ended is made too early ($\Delta t$ too short), avalanches will be terminated prematurely; if the $\Delta t$ chosen is too long, avalanches will be falsely concatenated. If avalanches did simply propagate like a wave, an approximation for Δt (Δt$_{avg}$) could be obtained by averaging the time between one nLFP at one electrode and the next nLFP at neighbouring electrodes only. Because nLFPs in avalanches occur in irregular patterns across electrodes on the array, a pair wise approximation can be used in order to assess the average time that is required for nLFPs to propagate between electrodes.

In order to calculate Δt$_{avg}$, the distribution of time intervals T for successive nLFPs on the array can be obtained. Starting with the first nLFP, e.g. A$^k$(t$_i$) on electrode k at time t$_i$, the next occurrence of an nLFP on the array can be searched for, e.g. A$^l$(t$_j$) on electrode l at time t$_j$, and calculated the time interval T$_{m\cdot\Delta t}^{k,l}$, where m=(t$_j$−t$_i$)/Δt. This process can be repeated for all occurrences of nLFPs on electrode k and for all electrodes. The resulting values can be combined into one density distribution P(T$_{m\Delta t}$), which captures how often successive nLFPs occurred with a particular delay m·Δt on the array irrespective of their spatial location. Consequently, the average value of T provides an approximation for Δt$_{avg}$, the average time to wait before making a decision whether an nLFP propagated on the array. However, this interval distribution is highly skewed, particularly when one compares the last nLFP with the first nLFP in successive avalanches that are separated by long times. In order to exclude time intervals from successive nLFPs that are barely correlated, a cut-off time τ$_{max}$ can be calculated for which the average crosscorrelation function (ccf) for pair wise electrode comparisons R$_{ccf}$(τ) had decayed to negligible values. The ccf between electrodes k, l (R$_{ccf}^{k,l}$(τ)) can be calculated as $$R_{ccf}^{k,l}(\tau) = \frac{\frac{1}{m_{max}}\sum_{m=1}^{m_{max}} A'^k_{LFP}(m\cdot\Delta t + \tau)A'^l_{LFP}(m\cdot\Delta t)}{\sigma(A'^k_{LFP})\sigma(A'^l_{LFP})}, \quad (1)$$

at Δt=1 ms for τ∈[−100,100], where m is an integer value up to m$_{max}$·Δt+τ<T$_{tot}$, A'$^k$(t$_i$)=A$^k$(t$_i$)−E(A$^k$), E(.) is the expected value for A$^k$(t$_i$), and σ$^2$(.) is the variance. Finally, the population ccf (R$_{ccf}$(τ)) can be calculated as $$R_{ccf}(\tau) = \frac{2}{n_{elec}(n_{elec}-1)}\sum_{k=1}^{n_{elec}}\sum_{l=k+1}^{n_{elec}} R_{ccf}^{k,l}(\tau) \quad (2)$$

The estimate of the average time between successive, correlated nLFPs on the array, i.e. Δt'$_{avg}$, can be obtained by integrating the density distribution of intervals for each network up to τ$_{max}$, $$\Delta t'_{avg}(\tau_{max}) = \sum_{m=1}^{m\cdot\Delta t=\tau_{max}} T_{m\Delta t} P(T_{m\cdot\Delta t}) \quad (3)$$

Because the exemplary maximal sampling rate was 1 kHz, the actual Δt$^{avg}$ to calculate avalanches can be taken as the nearest multiple of Δt=1 ms. In short, after Δt$_{avg}$ was calculated for a particular network and experimental condition, the extracellular signals v(t) can be re-sampled at the new temporal resolution of Δt$_{avg}$. Time and amplitude of nLFP peaks can be extracted as A$^k$(t$_i$), where t$_i$=i·Δt$_{avg}$, i∈[1, n'$_{max}$] and T$_{tot}$=n'$_{max}$·Δt$_{avg}$. Avalanches can be determined on the down-sampled data set at bin width Δt$_{avg}$.

Figure 3:
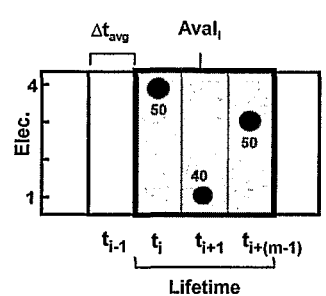
FIGS. 3 A-C illustrate the spatiotemporal organization of nLFPs induced by co-application of dopamine and NMDA.
Figure 3:
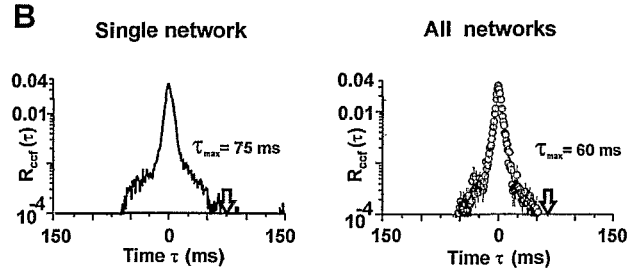
Figure 3:
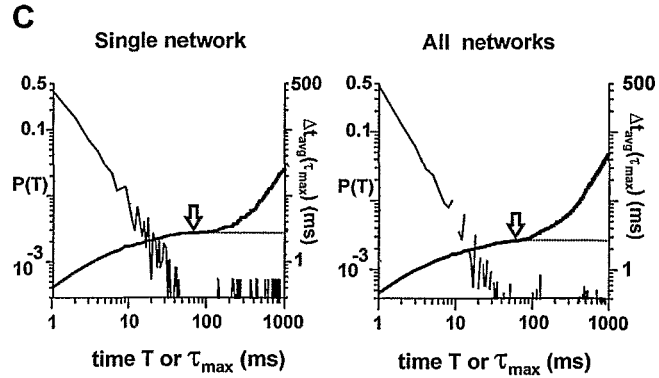

FIG. 3 illustrates the derivation of neuronal avalanches at the correct temporal resolution Δt$_{avg}$ using avalanche activity induced by co-application of dopamine and NMDA in an acute medial prefrontal cortex slice from an adult rat. A, Neuronal avalanches are defined on a sequence of consecutively active time bins of width Δt$_{avg}$, bracketed by at least one time bin with no activity. Sketch of an avalanche of size s$_{ele}$=3 electrodes, size s$_{LFP}$=140 μV, and lifetime m=3·Δt$_{avg}$ on a 2×2 electrode array (absolute nLFP amplitudes A$^k$(t$_i$) indicated by dot diameter and numbers in μV). B, nLFPs at different electrodes are strongly clustered in time as demonstrated by the average crosscorrelation function R$_{ccf}$. Left: single slice; average from 595 pair wise cross correlations. Right: Average from all n=6 acute rat slices encompassing 6824 correlation functions (30 μM dopamine and 3 μM NMDA). Note that R$_{ccf}$ decays to negligible levels within ±100 ms. τ$_{max}$ is indicated by arrows for which R$_{ccf}$ dropped below 10$^{-4}$. C, Derivation of average bin width Δt$_{avg}$ for neuronal avalanche analysis. Corresponding change in average inter-nLFP interval (thick size; right axis) from all electrode pairs, i.e. Δt$_{avg}$ as a function of upper cut-off for integration time τ$_{max}$. The inter-nLFP interval distribution is plotted on the left axis (thin line). For the single slice (left), R$_{ccf}$(τ$_{max}$)<10$^{-4}$ for τ$_{max}$ for τ$_{max}$=75 ms, and Δt$_{avg}$(τ$_{max}$)= 2.7 ms. For all slices (right), R$_{ccf}$(τ$_{max}$)<10$^{-4}$ for τ$_{max}$=60 ms and Δt$_{avg}$(τ$_{max}$)=2.7 ms (mean±S.E.M.). Note plateau reached for Δt$_{avg}$ at τ$_{max}$ (arrows). In general, Δt'$_{avg}$ varies very little for τ$_{max}$ between 50-100 ms for single networks as well as for the population of networks. Dotted line indicates read-out of Δt$_{avg}$.

C. Avalanche Size Distributions

Avalanche sizes can be calculated in two different ways (see also FIG. 3A). By taking into account nLFP peak amplitudes A$_i^k$, the avalanche size s$_{LFP}^{Aval_j}$ can be calculated by summing up A$_i^k$ on active electrodes for the lifetime T$^{Aval_j,LFP}$=m Δt$_{avg}$ of Aval$_j$, defined as the number of bins m of width Δt$_{avg}$ that were occupied by avalanche Aval$_j$ that started at time t$_i$ and stopped at time t$_i$+(m−1)·Δt$_{avg}$ $$s_{LFP}^{Aval_j} = \sum_{i=0}^{m-1}\sum_{k=1}^{n_{elec}} A_{t_i+m\cdot\Delta t_{avg}}^k. \quad (4)$$

For the density distribution of s$_{LFP}$, the range in sizes s$_{LFP}$ was covered by 100 bins that increased logarithmically from 3-300 μV, which results in equidistant sampling of the data in logarithmic coordinates. Avalanche sizes can also be calculated as the number of active electrodes within an avalanche, s$_{ele}$, using (4), but setting all non-zero A$_i^k$ values to 1. For the density distribution of s$_{ele}$, linear binning from 1-100 can be used. In the critical state, the distribution of avalanche sizes forms a power law with slope α=−3/2. From the experimental data, the exponent a of the power law represents the slope of the log-log transformed size distribution and can be estimated using linear regression analysis. Estimating α is not limited to regression analysis only. For example, α can be estimated using a maximum likelihood estimation $$-\alpha = 1 + n\left[\sum_{i=1}^{n}\ln\frac{N(s_i)}{N(s_{min})}\right]^{-1} \quad (5)$$

where $N(s_i)$ represents the number of avalanches of size $s_i$, $N(s_{min})$ represents the number of minimal avalanche size $s_{min}$ measured, and n represents the number of size categories. Alternatively, $\alpha$ can be estimated from the cumulative size distribution, which forms a slope of $\alpha+1$. Because no significant differences exist between estimates of et based on $s_{LFP}$ ($\alpha_{LFP}$) or ($s_{ele}$) ($\alpha_{ele}$) slope values can be given as $\alpha_{LFP}$ unless a particular emphasis is placed on the area an avalanche covers on the array. Average avalanche size distributions can be plotted as mean±S.E.M. In FIGS. 2D,E the avalanche size distributions obtained at $\Delta t_{avg}$ for $s_{LFP}$ and ($s_{ele}$) are plotted in log-log coordinates. Both distributions reveal a power law with slope $\alpha_{LFP}$ and $\alpha_{ele}$ of ~−1.5 as determined by linear regression (exact numbers and regression line are given in the figure; average from n=6 slices at 30 μM dopamine and 3 μM NMDA).

D. Avalanche Branching Parameter

The branching parameter $\sigma$ can be used to describe the balance of propagated synchronized activity in cortical tissue. The general definition of $\sigma$ refers to the ratio between successive generations, for example the average number of descendants from one ancestor. When $\alpha=-3/2$, the neuronal tissue is critical and correspondingly, $\sigma=1$. The branching parameter $\sigma$ can be defined in binary and analog terms.

In the binary case, $\sigma$ is defined as the average ratio of electrodes activated in time bin $\Delta t_{n+1}$ (descendants; $n_d$), divided by the number of electrodes active in time bin $\Delta t_n$ (ancestor; $n_a$). Mathematically, the average branching parameter $\sigma$ for the electrode array in the case of one ancestor electrode ($n_a=1$) is simply given by $$\sigma = \sum_{d=0}^{n_{max}} d \cdot p(d), \quad (6)$$

where d is the number of electrode descendants, p(d) is the probability of observing d descendants, and $n_{max}$ is the maximal number of active electrodes. Note that formula (6) does not describe a probability density and theoretically $\sigma$ can take any value $\geq 0$. In the binary case, $\sigma$ is best estimated from the first and second time bin of an avalanche. Although strictly speaking, $\sigma$ is only defined for one ancestor, $\sigma$ can also be estimated when there are multiple ancestors. Under these conditions, d is given by $$d = \text{round}\left(\frac{n_d}{n_a}\right) \quad (7)$$

where $n_a$ is the number of electrode ancestors observed in the first time bin and $n_d$ is the number of active electrodes in the second time bin of an avalanche and round is the rounding operation to the nearest integer. The likelihood of observing d descendants can be approximated by:

$$p(d) = \sum_{avalanches} \left(\frac{n_{\Sigma a|d}}{n_{\Sigma a}}\right) \cdot \left(\frac{n_{max}-1}{n_{max}-n_a}\right) \quad (8)$$

where $n_{\Sigma n|d}$ is the total number of electrode ancestors in all avalanches when $n_d$ descendants were observed, $n_{\Sigma a}$ is the total number of ancestors observed in all avalanches, and $$\left(\frac{n_{max}-1}{n_{max}-n_a}\right)$$

is a factor that provided an approximate correction for the reduced number of electrodes available in the next time bin because of electrode refractoriness. Note that the branching parameter is not defined for zero ancestors and thus does not provide information about the initiation of bursts. In cases where there is only one ancestor, formula (8) is equivalent to (6). In the analog case, the branching parameter $\sigma$ includes analog information about the LFP, e.g. its negative peak value (nLFP amplitude) or the nLFP area (integrated LFP amplitude from crossing negative threshold to return to threshold).

For the analog calculation, each nLFP in an avalanche is normalized to the amplitude or area of the first nLFP in the avalanche. For each time bin, the corresponding nLFP distributions from all avalanches can be combined. The succession of nLFP distributions during the life time of the avalanche then approximates the branching parameter $\sigma$. More specifically, if the mode (mod) of the nLFP distributions equals 1 for each time bin, nLFPs do not grow nor do they decay within an avalanche, which is equivalent to the binary case of $\sigma=1$. Because the distribution of ratios is better expressed in log values, in the analog case, one can state log(1)=0. Thus, log(mod)=0 demonstrates that the tissue is critical.

Figure 4:
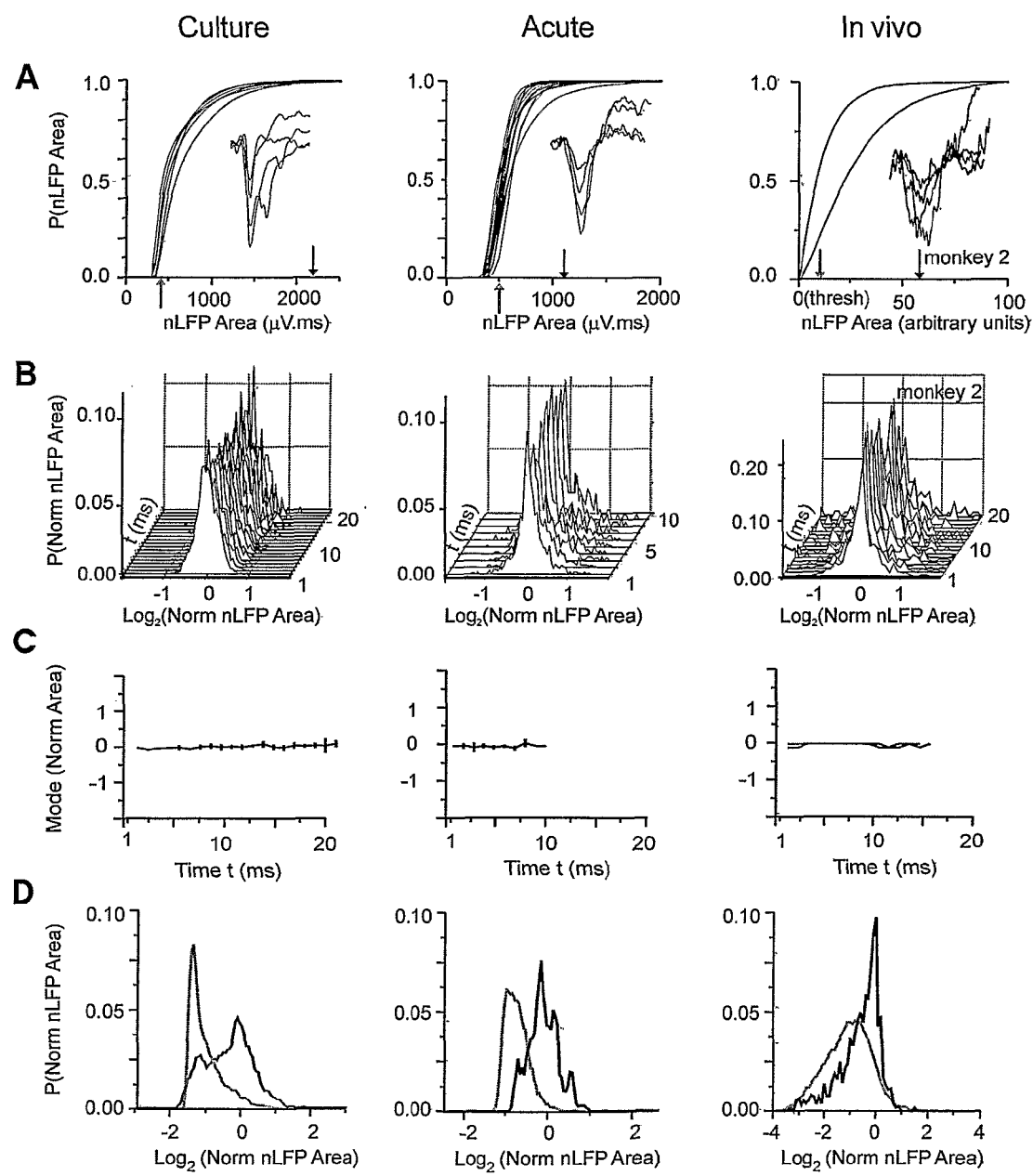
FIGS. 4 A-D illustrate the relationship of log (mod)=0 for three different experimental preparations.

An example of such a calculation is shown in FIG. 4, in which for three different experimental preparations this relationship of log(mod)=0 is demonstrated. For spontaneous activity in mature cortex slice cultures (FIG. 4, left), the acute mPFC slice from adult rats (FIG. 4, middle; cp. FIG. 2A), and the awake macaque monkey (FIG. 4, right) nLFP area varies widely as shown in the cumulative plots (FIG. 4A). However, nLFPs normalized to the corresponding first nLFP in each avalanche are centered at 0 demonstrating that within an avalanche, LFPs do not grow nor do they decay (FIG. 4B). This relationship is clearly demonstrated when plotting log (mode) for successive times within an avalanche (horizontal line at y=~0 in FIG. 4C). This relationship could not have occurred by chance; when nLFPs are randomly drawn from the population distribution for successive time steps within avalanches, the log(mod)=0 relationship is destroyed (in FIG. 4D).

E. Cluster Analysis of Avalanche Activity

Diverse avalanches can be grouped into families with similar spatiotemporal patterns. The grouping into families allows the determination of a family size distribution. In the critical state, the family size distribution reveals a heavy-tail with a slope gamma ($\gamma$) around ~−2.4 (FIG. 5F). This value of $\gamma$ can be used as a measure to characterize the critical state in the neuronal tissue.

A frame$_i$ can be defined as the 8×8 matrix of $A^k(t_i)$ at time $t_i$ at temporal resolution $\Delta t_{avg}$. In this case, the microelectrode array has a layout of 8×8. Because, in the example provided, corner electrodes on the microelectrode array were absent, a frame constituted a single pattern in a 60-dimensional space. An avalanche Aval$_j$ of lifetime $T^{Aval_j}=m \cdot \Delta t$ comprised of m frames and represented a vector in a m·60 dimensional space. The similarity Sim between two avalanches Aval$_i$ and Aval$_j$ in this space can be calculated using a correlation measure, which takes into account nLFP times as well as nLFP amplitudes. More precisely $$Sim(Aval_i, Aval_j) = \frac{\frac{1}{m \cdot 60}(Aval_i \cdot Aval_j) - E(Aval_i)E(Aval_j)}{\sigma(Aval_i)\sigma(Aval_j)} \quad (5)$$

where E(.) is the expected value, σ(.) is the standard deviation for individual vector values respectively, and $Aval_i \cdot Aval_j$ is the vector dot product. The similarity can range from −1 (perfectly anti-similar) to +1 (identical). The similarity measure can be expanded in order to measure similarities between avalanches with different lifetimes $T^{Aval_i} = m_i > T^{Aval_j} = m_j$. In the latter case, the avalanche $Aval_j$ with shorter lifetime can be shifted by up to $m_i - m_j$ steps. For each shift, the similarity can be calculated from the intersection of frames between the two avalanches and the final similarity can be assigned from the shift resulting in the highest similarity value. When combined into a similarity matrix, the diagonal of this matrix can indicate self-similarity, which has the maximal value of one (FIG. 5A).

Surrogate data sets with identical avalanche size and lifetime distributions can be obtained with 'paired-shuffling'. This shuffling method switches electrode assignments between randomly selected pairs of nLFPs recorded throughout the experiment on the array (FIG. 5D). It maintains the average rate of nLFPs at each electrode, the exact lifetime distribution, as well as the event size distribution and reduces type II errors (identifying similar avalanches when they could have occurred by chance). Each experimental data set can be compared against 100 surrogate data sets.

Significance of similarities between avalanches can be determined using surrogate data. A similarity distribution can be constructed from pair wise similarities between avalanches from 100 surrogate data sets. A Type I error of x % can be represented by finding the similarity threshold for which x % of similarities from the surrogate data sets were above this threshold.

Significant avalanche families can be identified by comparing the summed similarity among members within a family to that of surrogate data. However, this procedure might miss families with few members, i.e. small family size n, whose members have high similarity, or large families with members of relatively low similarity. Therefore, the average similarity among avalanches in a family ($Sim_{avg}^{Fam}$) can be compared to that from surrogate data. For example, the expected distribution of family size it and corresponding $Sim_{avg}^{Fam}$ can be obtained from 100 surrogate data sets. As can be seen in FIG. 5E, the incidence of small families with high $Sim_{avg}^{Fam}$ and large families with relatively low $Sim_{avg}^{Fam}$ is much lower in the surrogate data sets (white) compared to the original data set (grey). Families that occupied the parameter space outside the area taken up by 100 surrogate data sets can be considered significant. Thus, a significant family of size n in the original data set had either a higher $Sim_{avg}^{Fam}$ than all surrogate families of size n, or alternatively, all surrogate families had smaller sizes.

The recurrence of family sizes >10 beyond chance can be calculated and plotted as a function of dopamine concentration. First, for a given type I error, family size distributions can be calculated from the original data and corresponding 100 shuffled data sets. Then, the accumulated probability for families>size 10 can be calculated from each distribution. The ratio of these probabilities can provide an estimate of the encounter of a family size>10 beyond chance in the original data. The procedure can be repeated for different type I errors 0.1, 0.5, 1, 3, 5%. Values for different type I errors can be averaged and expressed in percentages. In general, the slope γ of the family size distribution is relatively robust for different type I errors (FIG. 5G).

Figure 5:
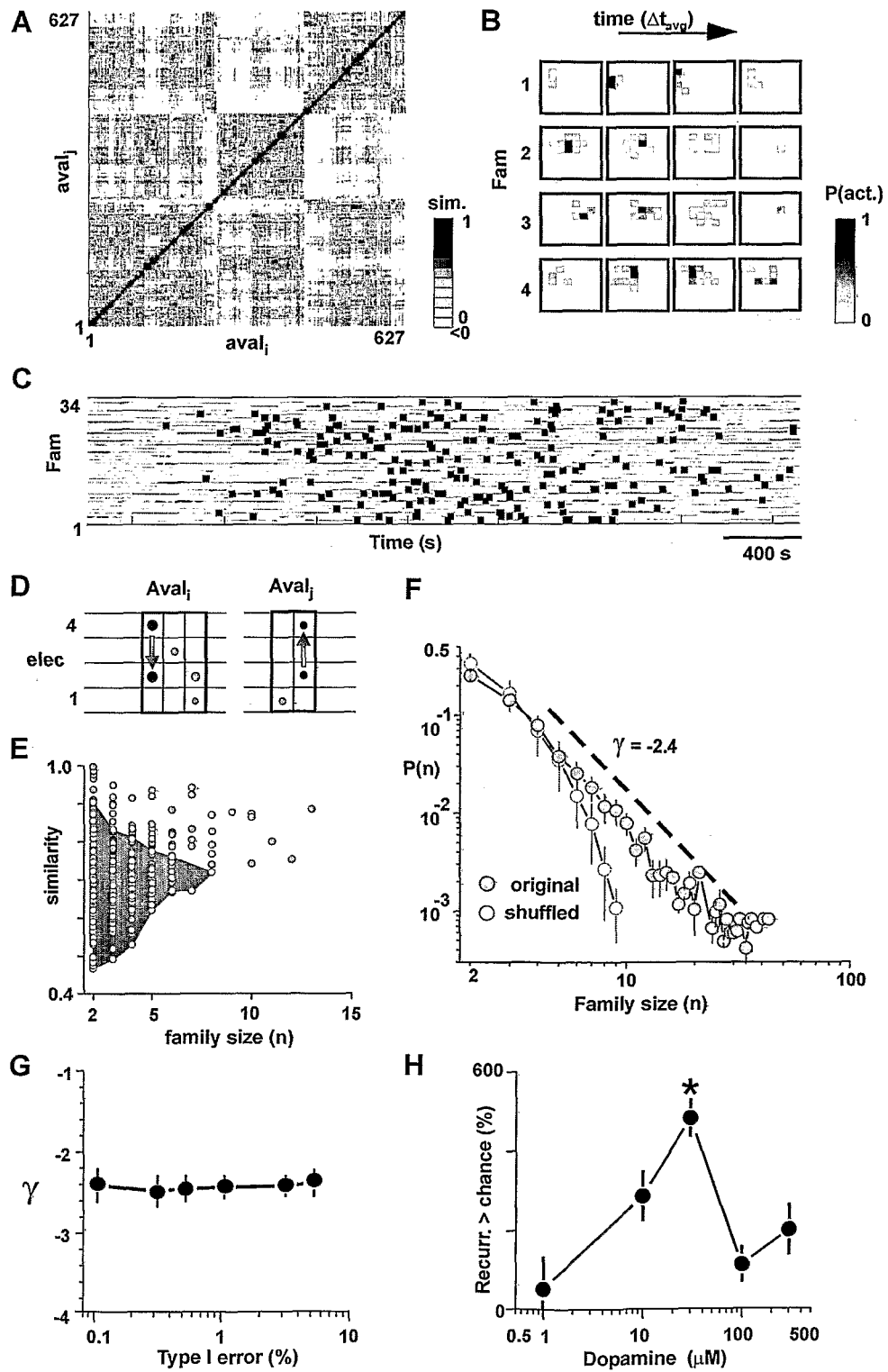
FIGS. 5 A-H illustrate an example of family clustering to determine the slope $\gamma$.

In FIG. 5, an example using the family clustering to determine the slope γ is demonstrated. The data are based on avalanche activity recorded from the experiments shown in FIG. 2 (acute rat mPFC slice, 30 μM dopamine and 3 μM NMDA). Spontaneous retrieval of avalanches is demonstrated to peak at moderate dopamine receptor stimulation and to be organized according to a power law with slope γ of −2.4±0.1. A, Sorted similarity matrix for 627 neuronal avalanches with lifetimes ranging from 2-9 times. Pairs of avalanches with high similarity are indicated by dark blue. The open red squares along the matrix diagonal indicate significant families with similar neuronal avalanche members (type I=5%; single experiment from FIG. 1A). B, Average spatiotemporal activation pattern for 4 significant families with at least 8 members from A. For each family, the average probability for an electrode on the 8×8 array to be active at time t (grayscale) is plotted for a period of around the main time of activity. C, Spontaneous recurrence of families (squares) is irregular and intermingled with other families (type I=5%; 34 families with lifetime≥2·$\Delta t_{avg}$ and >2 members shown; data from A). D, Surrogate data were constructed by pair wise shuffling of two electrodes in different bins. This maintains the lifetime as well as area distribution of avalanches, but destroys the spatiotemporal organization of activity within an avalanche. E, Scatter plot of family size n and average similarity within a family for original (gray) and shuffled (red) data. Significant families lie outside the boundary of the area covered by families from shuffled data sets algorithm. F, Family sizes n>3 are distributed according to a power law, γ=−2.4 (broken line). Average family size distribution (n=6), averaged over 6 different type I errors (gray circles; mean±S.E.M.; type I error=0.1, 0.3, 0.5, 1, 3, 5%; 30 μM dopamine and 3 μM NMDA; n=6 experiments). Families occur significantly more often than expected by chance as demonstrated by the expected family size distribution from 100 shuffled data sets per experiment for all type I errors (red line; mean±S.E.M.). G, The slope γ is independent of the type I error. Corresponding slope analysis from F for different type I errors. H, Recurrence of avalanche families follows an inverted-U shaped profile reaching ~500% higher levels than expected by chance (average for family sizes >6 from all networks for each concentration of dopamine combined with 3 μM NMDA).

E. Detailed Exemplary Embodiment

Figure 6:
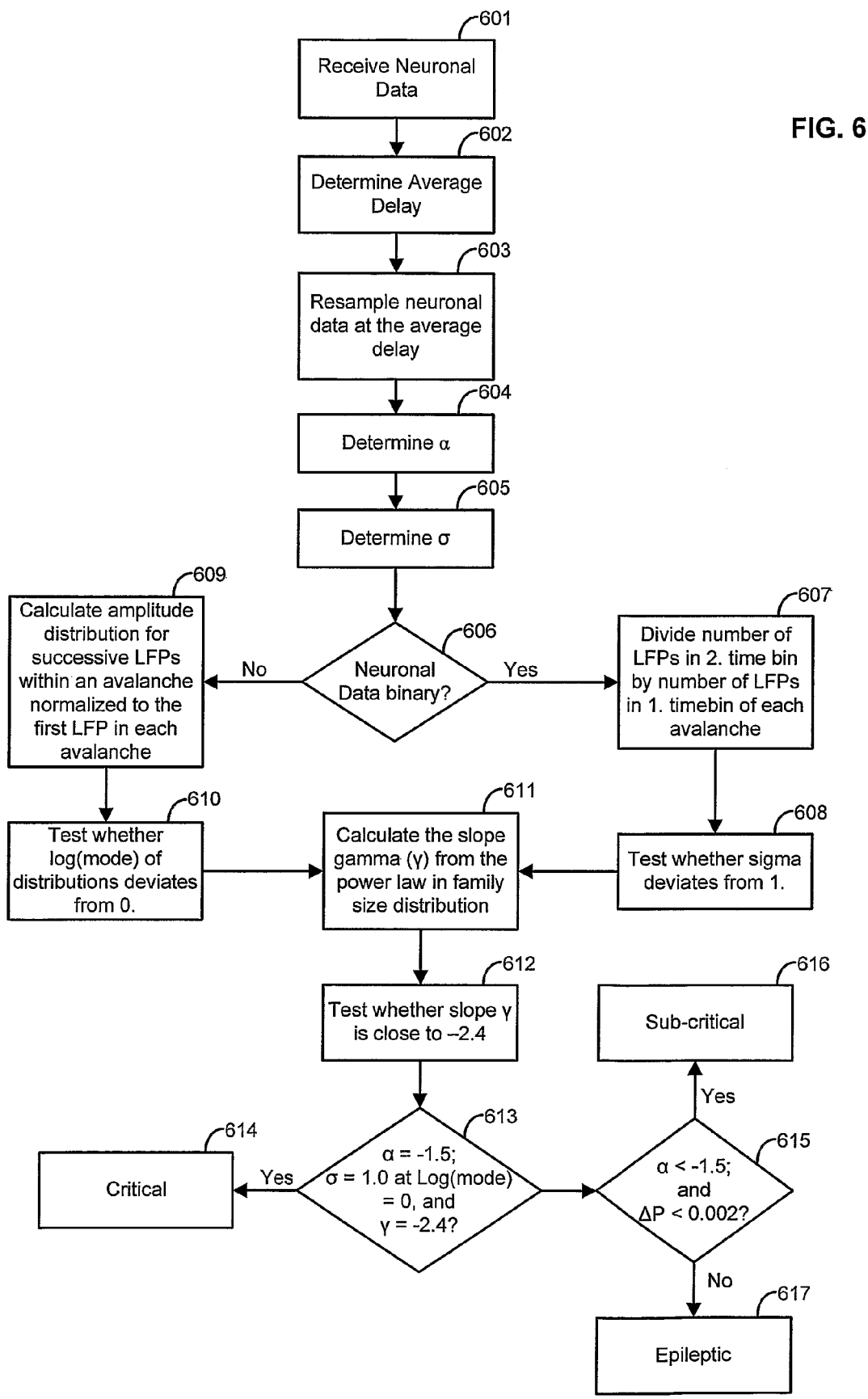
FIG. 6 is a flow diagram illustrating exemplary steps of a provided method.

To determine if a cortical network is in the critical state, spontaneous/evoked local field potential activity in superficial cortical layers can be recorded and analyzed. In one aspect, as shown in FIG. 6, extraction of the avalanche statistics can determine if a cortical network is in the critical state. At block 601, neuronal data can be received. At block 602, the average delay between successive LFPs in the network at highest temporal resolution can be determined ($\Delta t_{avg}$). This determination can be made, for example, using formulas 1-3. At block 603, the data can be resampled at the average delay ($\Delta t_{avg}$).

At block 604, a distribution of neuronal avalanche sizes can be calculated from binary or analog data using formula 4. Alpha (α) can be determined, for example, from the power law slope using linear regression.

At block 605, the branching parameter sigma (σ) can be determined. A determination can be made as to whether the data is binary or analog at block 606. If the neuronal data is binary, a can be determined using formula 6-9 at block 607. Then, at block 608, a test can be performed to determine if sigma deviates from 1. If the neuronal data is analog, amplitude distributions can be calculated for successive LFPs within an avalanche normalized to the first LFP in each avalanche, as described in herein, at block 609. Then, at block 610, a test can be performed to determine whether log(mode) of distributions deviates from 0.

Then at block 611, the slope gamma ($\gamma$) can be calculated from the power law in family size distribution. A test can be performed to determine whether slope $\gamma$ is close to −2.4 at block 612. At block 613, it can be determined if $\alpha=-1.5$ supported by $\sigma=1.0$ at log(mode)=0 and $\gamma=-2.4$. If that determination is met, declare the network as critical at block 614. If that determination is not met, proceed to block 615 to determine if $\alpha<-1.5$, $\sigma<1.0$, log(mode)<>0, and $\Delta P<0.002$. If that determination is met, declare the network sub-critical at block 616. If the determination is not met, in other words, if $\alpha<-1.5$, log(mode)>0, and $\Delta P>0.002$, declare the network epileptic at block 617.

In another aspect, provided is a method for determining a cognitive enhancement and/or anti-epileptic effect comprising detecting synchronized neuronal activity in neuronal tissue, monitoring spreading of the synchronized neuronal activity, determining a parameter indicative of the closeness of the synchronized neuronal activity to the critical state, and comparing the parameter to a predetermined value.

The parameter can be a slope of a size distribution of the synchronized neuronal activity and the predetermined value can be −3/2. The parameter can be a branching ratio of successively propagated synchronized neuronal activity and the predetermined value can be 1 or log(1)=0. If the slope is equal to the −3/2, the effect is optimal. If the determined slope is steeper than −3/2, the effect is sub-optimal. If the branching ratio is equal to 1, the effect is optimal. If the branching ratio is smaller or larger than 1 or deviates from log(1)=0, the effect is sub-optimal.

The step of detecting synchronized neuronal activity can utilize, for example, a micro-electrode array, magnetoencephalograph, electroencephalograph, imaging with fluorescent probes, and the like.

The synchronized neuronal activity can be, for example, local field potentials, magnetic currents, fluorescent probes, neuronal action potentials recorded as extracellular single or multi-unit activity, and the like.

The method can further comprise administering a composition suspected of having a cognitive enhancement and/or anti-epileptic effect to the neuronal tissue.

The composition effect can be, for example, dopaminergic, glutamatergic, GABAergic, cholinergic, serotonergic, noradrenergic, and the like.

In yet another aspect, provided is a method for determining a cognitive enhancement and/or anti-epileptic effect comprising detecting synchronized neuronal activity in neuronal tissue, monitoring spreading of the synchronized neuronal activity, determining a slope of a size distribution of the synchronized neuronal activity, comparing the slope of the size distribution to a threshold slope, determining a ratio of successively propagated synchronized neuronal activity, and comparing the ratio to a threshold ratio.

The threshold slope can be −3/2 and the threshold branching ratio can be 1. If the determined slope is equal to the threshold slope or threshold branching ratio, the effect is optimal. If the determined slope is steeper than the threshold slope, the effect is sub-optimal. If the determined branching ratio is equal to 1 or log(1)=0, the effect is optimal. If the determined branching ratio is smaller or larger than 1 or log(1)=0, the effect is sub-optimal.

The step of detecting synchronized neuronal activity can utilize, for example, a micro-electrode array, magnetoencephalograph, electroencephalograph, imaging with fluorescent probes, and the like.

The synchronized neuronal activity can be, for example, local field potentials, magnetic currents, single or multi-unit activity, fluorescent probes, and the like.

The method can further comprise administering a composition suspected of having a cognitive enhancement and/or anti-epileptic effect to the neuronal tissue.

The composition effect can be, for example, dopaminergic, glutamatergic, GABAergic, cholinergic, serotonergic, noradrenergic, and the like.

In a further aspect, provided is a method for screening compositions for a cognitive enhancement and/or anti-epileptic effect comprising applying a composition to neuronal tissue, measuring propagated synchronized activity in the neuronal tissue, determining a parameter indicative of the closeness of the synchronized neuronal activity to the critical state, and comparing the parameter to a predetermined value.

The step of detecting synchronized neuronal activity can utilize, for example, a micro-electrode array, magnetoencephalograph, electroencephalograph, magnetic resonance imaging, imaging with fluorescent probes, and the like.

The synchronized neuronal activity can be, for example, local field potentials, magnetic currents, single or multi-unit activity, fluorescent probes, and the like. The composition effect can be, for example, dopaminergic, glutamatergic, GABAergic, cholinergic, serotonergic, noradrenergic, and the like.

The parameter can be a slope of a size distribution of the synchronized neuronal activity and the predetermined value can be −3/2. If the determined slope is equal to the threshold slope or threshold ratio, the effect is optimal. If the determined slope is steeper than the threshold slope, the effect is sub-optimal.

The parameter can be a branching ratio of successively propagated synchronized neuronal activity and the predetermined value can be 1. If the determined branching ratio is equal to 1 or log(1)=0, the effect is optimal. If the determined branching ratio is smaller or larger than 1 or log(1)=0, the effect is sub-optimal.

III. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

Example 1 demonstrates that dopamine, a neurotransmitter involved in numerous cognitive and behavioural tasks, together with glutamate, the main excitatory neurotransmitter in the cortex, regulate the critical state in superficial layers of cortex.

i. Moderate Dopamine Receptor Stimulation Maximizes Recurrence and Distance of Spatial Correlations in Neuronal Avalanches.

Figure 7:
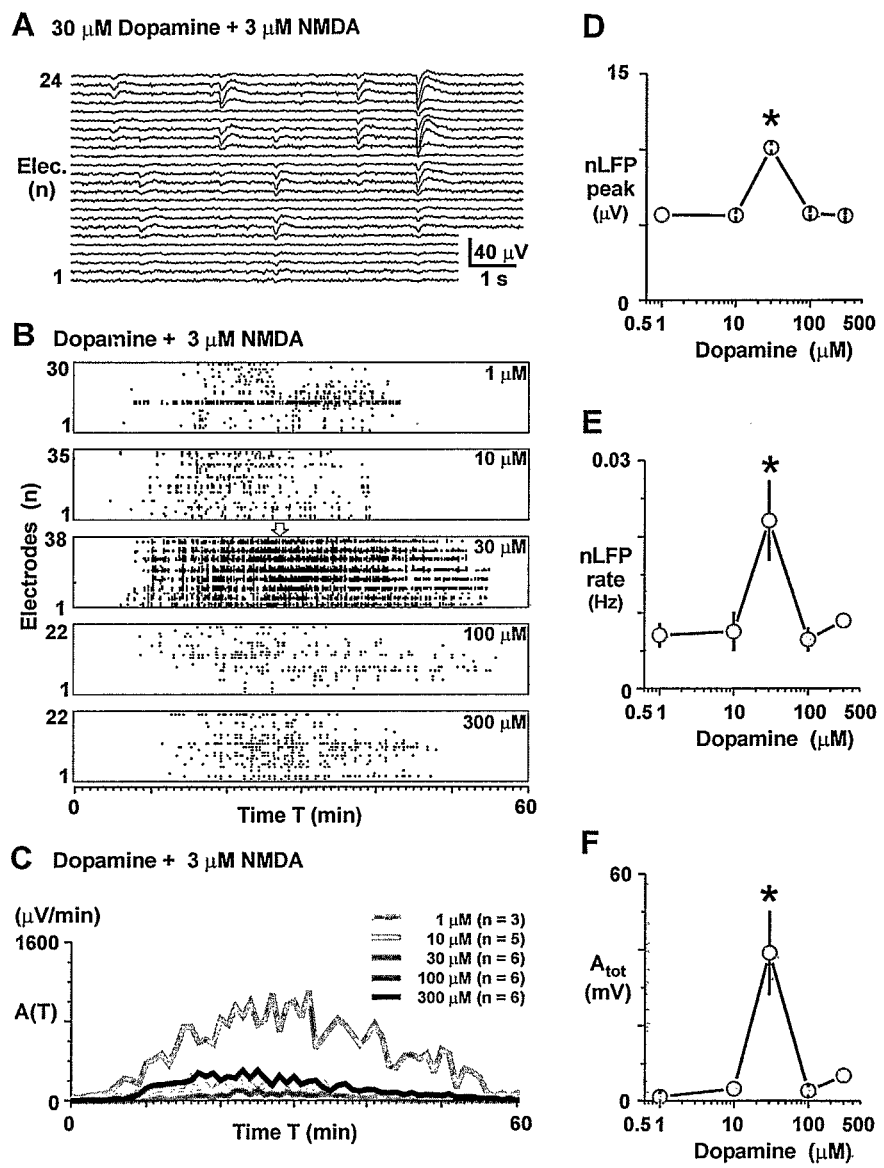
FIGS. 7 A-F illustrate an inverted-U profile for the induction of spontaneous LFP activity by dopamine in acute slices of rat mPFC in the presence of NMDA.

Acute coronal slices of medial prefrontal cortex (mPFC) were taken from adult rats and placed on planar microelectrode arrays. Extracellular neuronal activity was recorded simultaneously from superficial and deep layers of mPFC and up to 1.8 mm along layers (FIGS. 2A,B and FIG. 7). While slices were not spontaneously active in normal ACSF, bath-application of dopamine in combination with 3 µM of the glutamate N-Methyl-D-Aspartate (NMDA)-receptor agonist NMDA induced spontaneous extracellular activity that increased over the course of ~30 min after which the activity slowly tapered off (FIG. 7A-C). The activity at single electrodes was composed of individual LFP events characterized by a sharp (10-50 ms) negative peak followed by a brief positive deflection. These nLFPs revealed an inverted-U dependence on the dopamine concentration; the mean nLFP peak, the rate of nLFPs per electrode, as well as the total activity, $A_{tot}$, i.e. sum of nLFP peak amplitudes, were maximal at moderate concentration of dopamine (30 µM) and were significantly reduced at dopamine concentrations higher or lower than 30 µM (FIG. 7B-F; peak: $DF_{4,21}=14.7$; p=0.005; rate: $DF_{4,21}=9.7$; p=0.046; $A_{tot}$: $DF_{4,21}=15.0$; p=0.005). In contrast, the number of active electrodes (33±4 electrodes) and the duration of spontaneous activity (43±3 min) were similar for each condition (n=26 slices; p>0.05).

FIG. 7 illustrates an inverted-U profile for the induction of spontaneous LFP activity by dopamine in acute slices of rat mPFC in the presence of NMDA. A, Bath-application of 30 µM dopamine and 3 µM NMDA gives rise to spontaneous nLFPs characterized by sharp negative peaks followed by a transient depolarization (acute rat MPFC slice, 24 most active electrodes shown; cp. FIG. 2B). B, Representative raster displays of nLFP activity on the microelectrode array for 5 different concentrations of dopamine when combined with 3 µM NMDA. Dots represent times of negative nLFP peaks. Drugs were applied at t=0 and were present throughout the experiment. Arrow indicates time period shown in A. C, Corresponding average time course of spontaneous nLFP activity as a function of the dopamine concentration when co-applied with 3 µM NMDA (number of experiments given in brackets). Highest activity levels were obtained with 30 µM dopamine. D-F, Corresponding dose-response relationship for average negative nLFP peak, nLFP rate at single electrodes, and total activity $A_{tot}$ on the array.

Since it was determined that activity at single cortical sites was dependent on the dopamine concentration, it was determined whether a similar relationship governed the spatiotemporal organization of nLFPs on the array. When first studying the temporal organization only, it was evident from visual inspection of the spontaneous activity on the array, nLFPs were highly clustered across electrodes. This was quantified using crosscorrelation analysis for pairs of electrodes. The average crosscorrelation $R_{ccf}$ (formula 2; cp. FIG. 3B) peaked significantly and decayed to negligible values within ~100 ms, again, without indication of strong oscillatory activity. Thus, spontaneous activity in the cortical slices was composed of irregularly occurring spatiotemporal nLFP clusters.

These clusters suggested that the spontaneous activity might be composed of neuronal avalanches as described previously in organotypic cultures and acute slices from somatosensory cortex. When analyzing the activity for neuronal avalanche organization, it was found that only at 30 ELM dopamine, at which nLFP occurrence was highest, that the distribution of concatenated nLFPs revealed a power law in cluster sizes with slope of $\alpha=-1.5$ (FIG. 8, cp. FIGS. 2D,E).

This finding held true whether α was calculated by summing nLFP amplitudes within an avalanche ($\alpha_{LFP}=-1.50\pm0.03$; $s_{LFP}=6-300$ µV; R=-0.99), or when counting the number of active electrodes in an avalanche ($\alpha_{ele}=-1.47\pm0.03$; $s_{ele}=1-18$ electrodes; R=-0.996; FIGS. 2D,E). At this concentration, the optimal bin width $\Delta t_{avg}$ was 2.7±0.2 ms (FIG. 3C), which translated into a propagation velocity of ~74 mm/s for nLFPs on the array at an inter-electrode distance of 200 µm.

At dopamine concentrations lower or higher than 30 µM, the distribution of concatenated nLFPs revealed a cluster size distribution with a steeper slope a close to -2 that was significantly different from -1.5 (FIGS. 8A,B; $DF_{5,215}=156.8$, p<0.0005). These differences could not have resulted from differences in $\Delta t_{avg}$, which was similar for all dopamine concentrations tested ($DF_{4,21}=0.98$; p=0.44; 2.7±0.1 ms average for all n=26 experiments). Similarly, the distributions of cluster sizes obtained for different dopamine concentrations did not change much in shape as indicated by the high regression coefficient R for all conditions (R=0.96-0.99). Finally, in accordance with the finding on nLFP rate for single electrodes, the avalanche rate was also maximal at moderate dopamine concentrations, although not statistically significant (FIG. 8C; $DF_{4,21}=7.0$; p=0.13).

Figure 8:
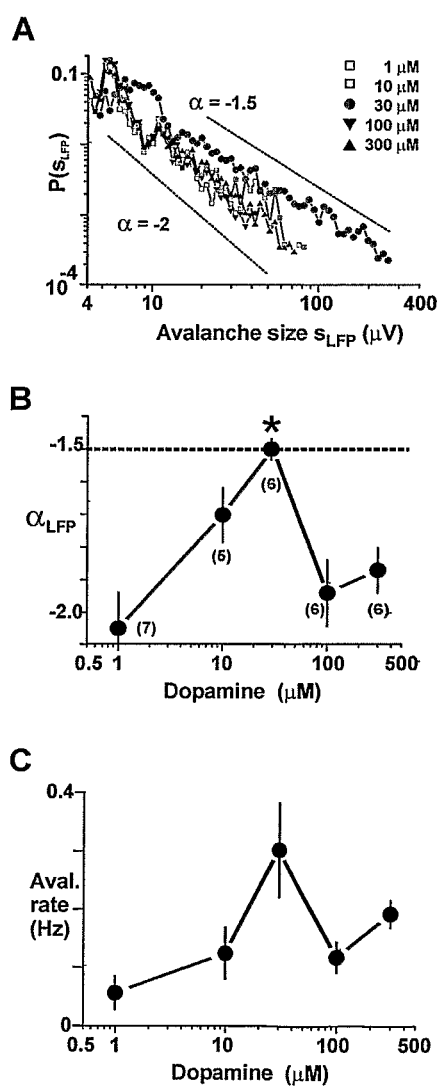
FIGS. 8 A-C illustrate an inverted-U pharmacological profile for avalanche induction by dopamine.

FIG. 8 illustrates an inverted-U pharmacological profile for avalanche induction by dopamine. A,B, An inverted-U shaped pharmacological profile for the slope a characterizes neuronal avalanche induction by dopamine in the presence of NMDA. The maximal slope of $\alpha=-1.5$ is reached at a concentration of 30 µM dopamine (mean R=-0.92; regression taken from size=4-200 µM; p<0.0005). The slope α is significantly more negative at lower and higher concentrations of dopamine (mean±S.E.M.). Numbers in brackets give the number of experiments for each condition. C, Corresponding dose-response relationship for avalanche rate.

Provided is a precise and quantitative description of an inverted-U shaped pharmacological profile for NMDA-dopamine interaction at the network level Moderate NMDA and dopamine receptor stimulation induces avalanches with a maximal slope of $\alpha=-1.5$ in avalanche size distribution and maximizes the spontaneous formation and retrieval of avalanches. A slope of $\alpha=-1.5$ is the maximal slope attainable within the wide range of dopamine concentrations tested. This inverted-U profile for α has important implications for the formation of spatiotemporal patterns in superficial cortex layers. Because $\alpha_{LFP}$ and $\alpha_{ele}$ quantify the occurrence of large avalanches relative to smaller avalanches, α provides a direct measure of the number and the extent of spatial correlations formed within the network. More specifically, at 30 µM dopamine, the maximal area $s_{ele}$ within the power law regime was ~18 electrodes (FIG. 2E), which is equivalent to a spatial extent of about 850×850 µm². Accordingly, a slope smaller than -1.5 indicates a relative reduction in large nLFP clusters, i.e. long-range correlations that link distant sites in the network.

The neuromodulator dopamine moves the network into the optimal state in line with an increase in overall activity. Several aspects of the recurrence rate inside and outside the optimal state as measured deserve particular attention. First, only the largest nLFPs will be recorded with planar microelectrodes from the bottom surface of the slice. While this does not affect much the estimate of the power law slope, it grossly underestimates the absolute rate of avalanches. For comparison, neuronal avalanche sizes range from 4-4000 µV in an organotypic cortex slice culture, where electrodes are directly adjacent to active neuronal tissue. By measuring only the range of the largest avalanches, e.g. from 400-4000 µV, which comprises about 6% of all avalanches, one would underestimate avalanche rate by about 94%. Second, the inverted-U profile leads to a relatively sharp drop in large avalanches. For example, at a slope value of −2 outside the optimal state, the recurrence of avalanches that are 100 times larger for any given avalanche size has dropped by a factor of 10 compared to a slope of −1.5, which is in addition to a strong reduction in spontaneous avalanche recurrence. In conclusion, sub-optimal dopamine-NMDA interaction results in a drastic decrease of avalanche recurrence as well as a decrease in spatial correlation when avalanches recur.

ii. Supralinear Dopamine $D_1$ and NMDA Receptor Interaction Mediates the Inverted-U Profile of Avalanche Induction PFC functions, e.g. working memory, depend in an inverted-U profile on the partial dopamine $D_1$ receptor agonist (+/−)-1-phenyl-2,3,4,5-tetrahydro-(1H)-3-benzazepine-7,8-diol hydrochloride (SKF38393). Similar to the dependence found for dopamine, SKF38393 induced neuronal avalanches by means of an inverted-U profile in the MPFC slices. Avalanches were robustly induced by bath-application of 3 μM NMDA and 3 μM SKF38393 (FIG. 9A; n=11). At 3 μM of the agonist, the $\Delta t_{avg}$ as well as the slope a was not significantly different from avalanche induction using 30 μM dopamine (FIG. 9B, C; $\Delta t_{avg}$=3.3±0.2; $\alpha_{LFP}$=−1.52±0.06; p>0.05). Importantly, the slope of α~−1.5 was achieved at a significantly reduced level of total activity compared to dopamine (p=0.007). This difference did not result from differences in avalanche rate (p=0.42), but rather from the reduced average nLFP peak amplitude in the presence of the agonist (6.62±0.01 mV; p=0.001). For concentrations of SKF38393 higher or lower than 3 μM, the slope a changed to steeper values than −1.5 (FIG. 9C; $DF_{3,206}$=39.1, p=0.0005) and avalanche rate and nLFP activity decreased (FIGS. 9D,E; rate: $DF_{3,31}$=11.09, p=0.012; $A_{tot}$: $DF_{3,31}$=10.1, p=0.018).

Figure 9:
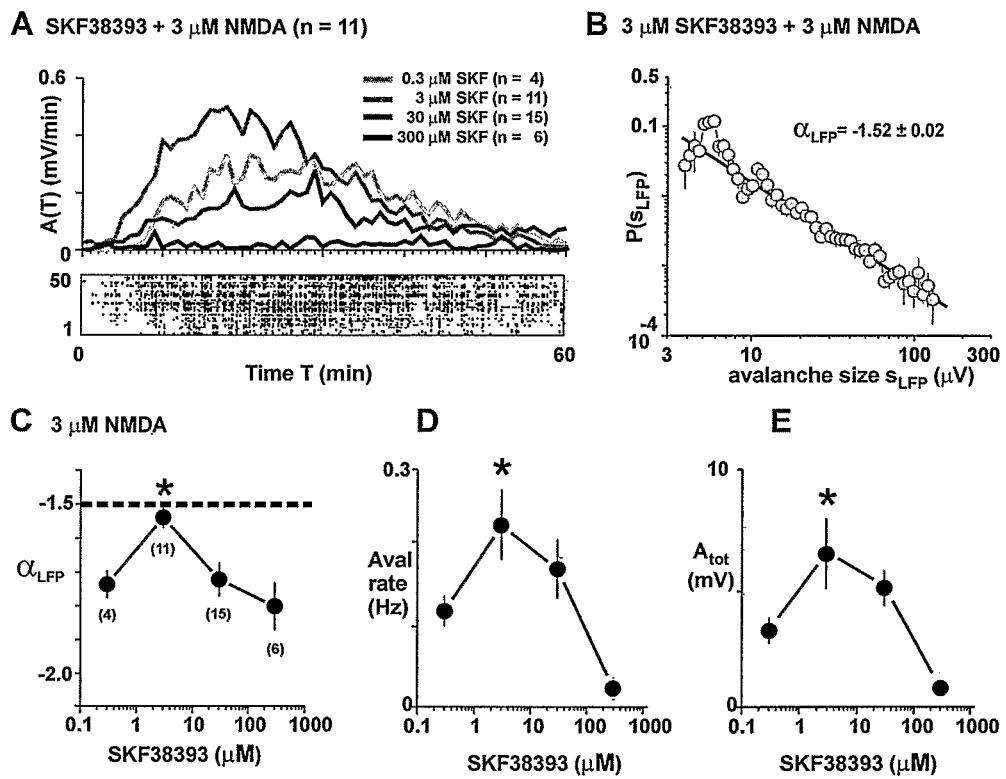
FIGS. 9 A-E illustrate dopamine $D_1$ receptor stimulation induces neuronal avalanches via an inverted-U shaped pharmacological profile.

FIG. 9 illustrates dopamine $D_1$ receptor stimulation induces neuronal avalanches via an inverted-U shaped pharmacological profile. A, Average time course of spontaneous nLFP activity for four concentrations of the dopamine $D_1$ receptor agonist SKF38393 ranging from 0.3-300 μM bath-applied in combination with 3 μM NMDA (number of experiments in brackets). Bottom: Raster plot of nLFPs for a single, representative network at 3 μM of the agonist. B, Corresponding distribution in avalanche sizes $s_{LFP}$ (mean±S.E.M.). C, The $D_1$ agonist SKF38393, when co-applied with 3 μM NMDA, mimics the inverted-U shaped pharmacological profile for the slope a obtained with dopamine. The slope is maximal at 3 μM of SKF38393 and decreases at lower and higher concentrations (mean R=−0.92; size=4-200 μV; p<0.0005). Numbers in brackets give the number of experiments for each condition. D, Corresponding dose-response relationship for avalanche rate and (E) total activity.

In accordance with the co-dependence of PFC functions on NMDA and dopamine $D_1$ receptor stimulation, co-stimulation of the dopamine $D_1$ and NMDA receptor was required for avalanche induction. Bath-application of 3 μM SKF38393 alone did not induce nLFPs or avalanches, however, avalanches were rescued when 3 μM NMDA was added ($\alpha_{LFP}$=−1.55±0.07; R=−0.95; FIGS. 10A,B). At a concentration of 10 μM, the dopamine $D_1$ receptor antagonist R(±)-7-chloro-8-hydroxy-3-methyl-1-phenyl-2,3,4,5-tetrahydro-1H-3-benzazepine hydrochloride (SCH23390) blocks numerous dopamine and $D_1$-mediated effects in PFC at the single neuron level in vitro. Accordingly, bath-application of 3 μM NMDA alone induced negligible nLFP and avalanche activity in the presence of SCH23390 (10 μM; FIG. 10C; n=7). Finally, avalanche induction was completely blocked by 10 μM SCH23390 in the presence of 30 μM dopamine and NMDA, suggesting that it is indeed the dopamine $D_1$-receptor which is crucial for avalanche induction (FIGS. 10D,E; n=8; αLFP=−1.55±0.06 for washout; R=−0.98).

Figure 10:
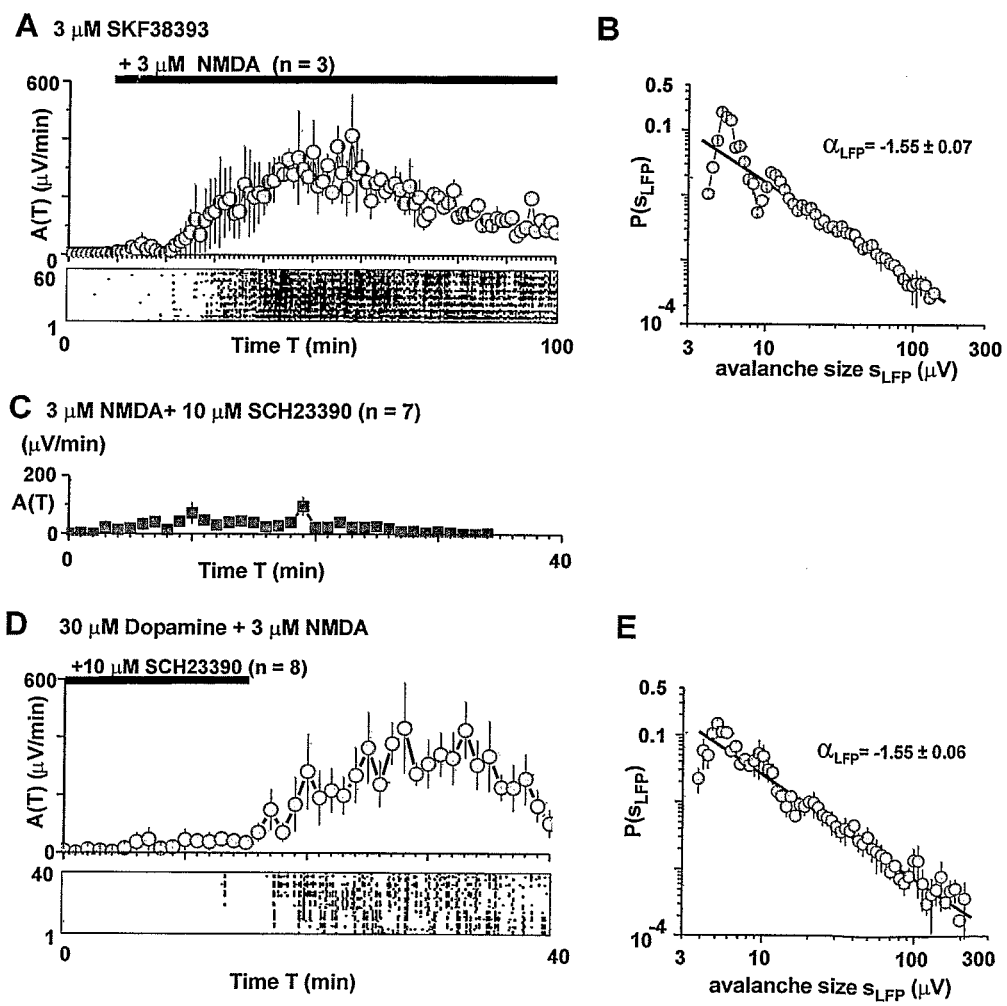
FIGS. 10 A-E illustrate that avalanche induction requires co-activation of the NMDA and dopamine $D_1$ receptor.

FIG. 10 illustrates that avalanche induction requires co-activation of the NMDA and dopamine $D_1$ receptor. A, Dopamine $D_1$ receptor stimulation with SKF38393 (3 μM) alone does not induce avalanches, but avalanche activity is rescued by additional application of 3 μM NMDA. Bottom: Raster plot of nLFPs for a single, representative network. B, Corresponding avalanche size distribution for experiments shown in C (solid line: linear regression). C, Bath-application of 3 μM NMDA does not induce neuronal avalanches when the dopamine $D_1$ receptor is blocked. D, The ddpaine $D_1$ receptor antagonist SCH23390 (10 μM) prevents induction of neuronal avalanches by 30 μM dopamine and 3 μM NMDA. Avalanche activity is rescued upon washout of SCH23390. Bottom: Raster plot of nLFPs for a single, representative network. E, Corresponding avalanche size distribution for recovery (solid line: linear regression).

This control of neuronal avalanche formation provides a coherent network level representation for many robust actions of dopamine and NMDA at the single cell level in PFC. First, $D_1$ receptor stimulation, through up-regulation of NMDA responses, increases the overall excitability of the cortical network, which is in line with the increase in spontaneous avalanches observed when 3 μM NMDA is co-applied with a dopamine $D_1$ receptor agonist, but not otherwise. Second, $D_1$ receptor stimulation, by reducing intrinsic potassium currents, allows neurons to respond faster to synaptic inputs, which is in accordance with the fast, propagation of neuronal activity that constitutes an avalanche. Third, dopaamine $D_1$ receptor stimulation does not inhibit, but instead facilitates fast glutamatergic transmission in cortical pyramidal neurons, which supports the fast successive activation of neurons that underlies avalanche formation. Finally, dopamine $D_1$ receptor stimulation depolarises cortical interneurons and strengthens synaptic coupling between pyramidal neuron input and interneuron spiking. This effect of dopamine increases the amplitude and temporal precision of inhibition in cortex in support of the formation of synchronized activity in the network. This interpretation is in line with the ability of dopamine and NMDA to induce sharp nLFPs indicative of synchronized activity, which were blocked when fast synaptic inhibition was reduced. How precisely fast inhibition contributes to avalanche formation can require the identification of the cell types and intracellular activity with respect to nLFP generation.

The concentration dependence of avalanche formation also agrees well with the effects of dopamine and NMDA at the single cell level. Optimal avalanche induction and pattern retrieval can be achieved at 30 μM of dopamine, a concentration at which dopamine robustly depolarises PFC fast-spiking interneurons and modulates GABAergic and glutamatergic inputs to PFC pyramidal neurons in addition to affecting other single neuron properties. The reduction of avalanches at higher concentrations of dopamine and SKF38393 is consistent with the reduction of NMDA evoked currents and postsynaptic potentials in pyramidal neurons at high concentrations of dopamine and a dopamine D1-agonist. It is also in line with the finding that local pressure ejection of DA (100 μM-10 mM) or SKF38393 (100 μM) decreases the reliability and amplitudes of excitatory transmission in prefrontal circuits, which should reduce the formation and size of avalanches. Similarly, the induction of avalanches at low concentrations of NMDA and dopamine D1-receptor stimulation supports the facilitation of NMDA currents at low concentrations of dopamine and SKF38393 (<10 μM; and the supralinear increase in PFC neuron excitability at these concentrations.

iii. Neuronal Avalanches are Localized to Superficial Cortex Layers

While in principle, synchronized activity can form in any cortical layer, however, provided are experiments that precisely demonstrate that neuronal avalanches are localized to superficial cortical layers only. Thus, the localization of recorded synchronized activity to superficial layers is an important aspect of the NAS-assay.

Although the microelectrode array covered all layers of mPFC, the occurrence of nLFPs was restricted to a smaller region on the array. When comparing light microscopic images of slices taken during recording with subsequent anatomical reconstruction of cortical layers based on Nissl stains (FIG. 11), it became clear that avalanche activity induced by co-application of 30 μM dopamine and 3 μM NMDA was strongest in superficial layers II/III, located at a cortical depth ranging from 200-900 μm (FIG. 11A-C). In contrast, activity was significantly less in deep layers V/VI (p<0.05, ANOVA; 30 μM dopamine and 3 μM NMDA). While there was also some variation in nLFP activity along superficial layers, these variations were relatively small compared to differences encountered between superficial and deep layers. The finding that avalanches are localized to superficial cortical layers was also confirmed for a cortical area different than the mPFC. Co-application of the dopamine $D_1$ receptor agonist SKF38393 (3 μM) and NMDA (3 μM) also induced neuronal avalanches primarily in superficial layers of acute somatosensory cortex slices from adult rats (FIGS. 11D,E).

Figure 11:
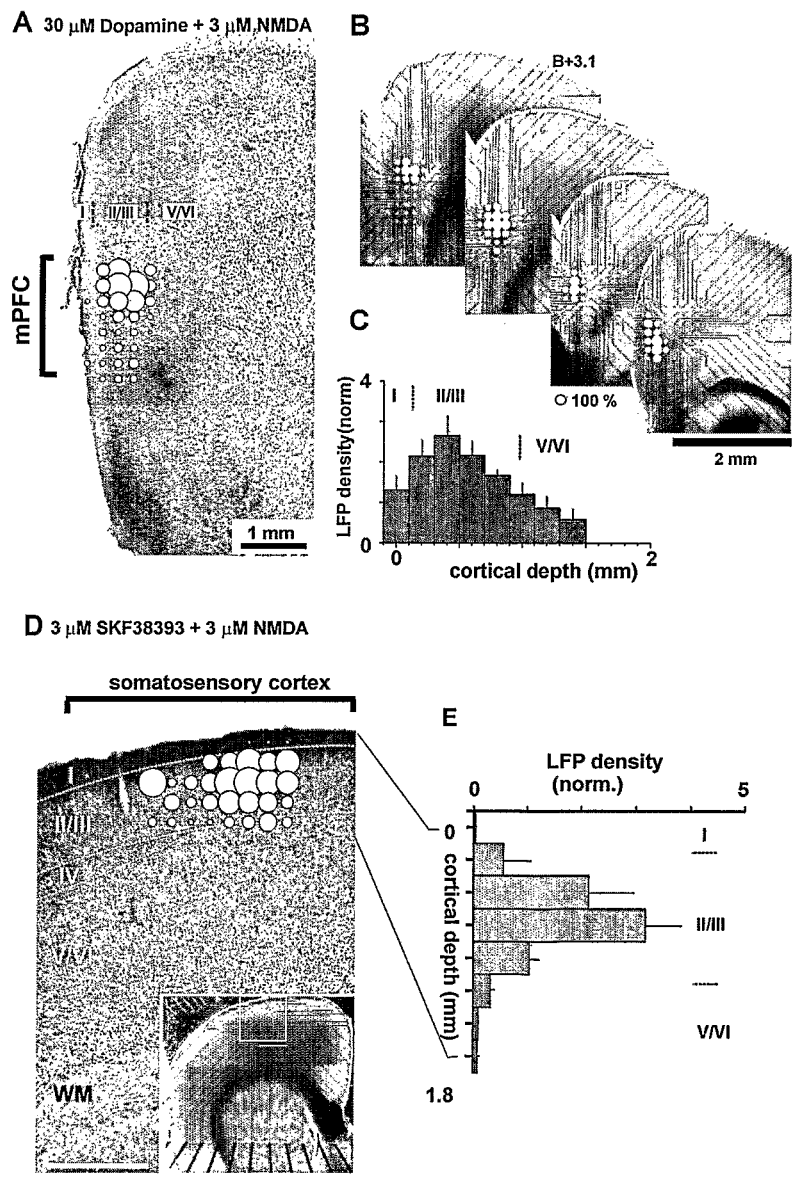
FIGS. 11A-E illustrate co-stimulation of the dopamine $D_1$ and NMDA receptor induces spontaneous avalanches predominantly in superficial layers of mPFC.

FIG. 11 illustrates co-stimulation of the dopamine $D_1$ and NMDA receptor induces spontaneous avalanches predominantly in superficial layers of mPFC. A, Overplot of a Nissl stained mPFC slice and nLFP density on the multielectrode array. B, Stacked montage of nLFP density at corresponding recording locations (bregma coordinates +4.2 to +3.1; light microscopic picture of the acute slice and multielectrode array position during recordings). Lines indicate electrode contacts. C, Average nLFP density as a function of cortical depth (n=6 experiments; 30 μM dopamine and 3 μM NMDA). D, Overplot of a Nissl stained somatosensory acute rat slice and nLFP density on the microelectrode array (avalanches were induced by 3 μM SKF38393, and 3 μM NMDA). Inset: light microscopic image during recording. E, Average nLFP density is highest in superficial layers II/III (n=6 somatosensory slices). Roman letters: layers; broken lines: average depths of layer borders iv. A Power Law Governs the Spontaneous Recurrence of Avalanche Families in PFC Provided is a quantitative and robust relationship for the highly diverse, yet stably recurring avalanche families in superficial layers. The recurrence of spontaneous spatiotemporal patterns reflects the organization of the underlying neuronal network and, in the presence of dopamine, regulates network connectivity. Avalanche recurrence in superficial layers represents preferred synaptic pathways that have been formed in the prefrontal cortex network thereby contributing to integrative and associative aspects of PFC functions.

Using an improved cluster algorithm, neuronal avalanches were grouped into families based on their similarities (FIG. 5). FIG. 5A shows how the spatiotemporal patterns of avalanches, when compared with each other, give rise to a sorted similarity matrix. In this matrix, avalanches with high similarities were grouped into families located along the matrix diagonal. When averaging avalanche patterns from individual families, different average spatiotemporal activity patterns were obtained that indicated the likelihood of a particular electrode being active when a family was activated (FIG. 5B).

The recurrence of a family was irregular and spread out in time intermingled with recurrences from other families (FIG. 5C). In order to better understand the organization of avalanche recurrences, i.e. family sizes n, family size distributions were plotted in double logarithmic coordinates (30 μM dopamine and 3 μM NMDA; n=6 slices). This revealed a power law-like distribution $P(n) \propto n^\gamma$ for significant families (size n>2) with slope $\gamma = -2.44 \pm 0.01$ (FIG. 5F; $R_{org} = -0.964 \pm 0.01$; n=6 slices). The slope γ, measured for all significant families, was robust for a wide range of different type I errors (FIG. 5G; 0.1%<type I<10%).

The statistical significance of a family recurrence was based on 100 surrogate data sets obtained with pair wise shuffling (FIG. 5D-F). The analysis for the corresponding surrogate data sets demonstrated the absence of large families as seen in the original data. Instead, the family size distribution for surrogate data decayed exponentially according to $P(n) = 0.21 \cdot e^{-0.34n}$ (R=−0.998), resulting in a downward pointing curve when plotted in double-logarithmic coordinates (FIG. 5F).

When comparing different concentrations of dopamine, an inverted-U shape profile characterized the likelihood that a family recurred beyond chance (FIG. 5H). In the presence of 3 μM NMDA, an optimal concentration of 30 μM of dopamine increased the likelihood of family recurrence by about ~500% beyond chance level ($DF_{4,21}=15.1$; p=0.0017).

xii. Spontaneous Recurrence of Neuronal Avalanches Requires Intact Fast GABAergic Synaptic Transmission The formation of sharp negative nLFP peaks and the fast propagation of activity, as identified in an avalanche, at first seem at odds with the slow action of dopamine and long-lasting NMDA currents. It was determined that while dopamine and NMDA receptor stimulation are necessary for avalanches to emerge, in addition, fast synaptic inhibition might be required to support the formation of synchronized activity, as has been-proposed from modelling studies.

Indeed, when fast synaptic GABAergic transmission was reduced in the mPFC slice by adding 10 μM picrotoxin, nLFP and avalanche activity ceased (FIG. 12A). Furthermore, picrotoxin prevented spontaneous avalanches induction altogether when co-applied with 3 μM NMDA and 3 μM SKF38393 (n=6; FIG. 12B), further demonstrating that spontaneous recurrence of neuronal avalanches required fast synaptic inhibition. Finally, spontaneous activity induced by bath-application of picrotoxin alone (10 μM) was significantly less compared to that achieved by 30 μM dopamine and 3 μM NMDA (FIG. 12C; $A_{tot}$: 5033±719 μV; nLFP rate: 0.01±0.001 Hz; avalanche rate: 0.18±0.02 Hz; duration: 28±2 min; all p<0.05; n=6). Importantly, the initial slope a of the disinhibited activity was smaller than −1.5 ($\alpha_{ele}=-1.97\pm0.02$; $s_{ele}=1-5$; $\alpha_{LFP}=-1.9\pm0.08$; $s_{LFP}=15-85$; p=0.001). Similarly, the maximal time difference between correlated electrodes on the array dropped significantly to $\tau_{max}=30.5\pm7.2$ (p=0.012), with a corresponding slight reduction in the $\Delta t_{avg}$ to 2.3±0.2 (p=0.07).

Figure 12:
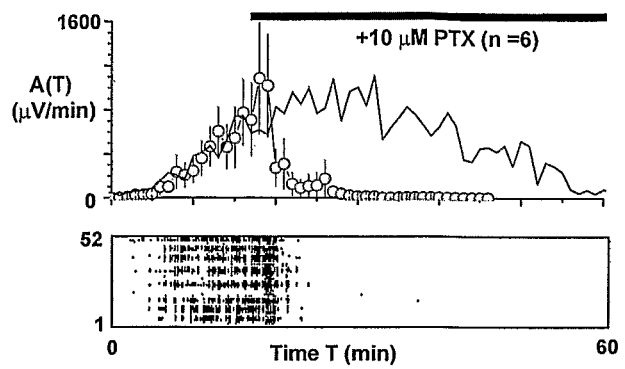
FIGS. 12 A-D illustrate neuronal avalanche recurrence depends on intact fast synaptic inhibition and differs from disinhibited spontaneous activity.
Figure 12:
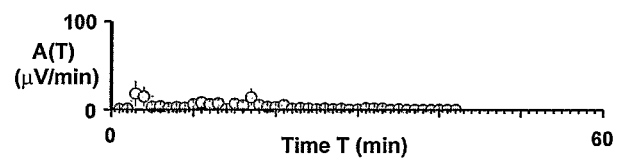
Figure 12:
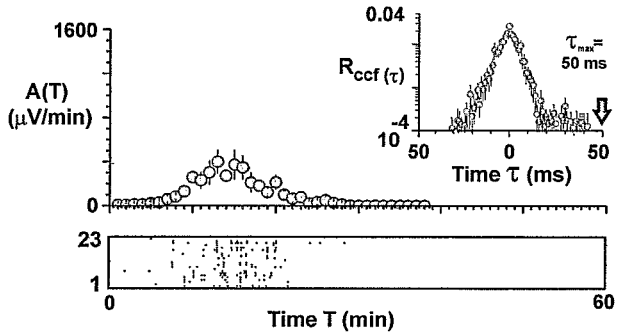
Figure 12:
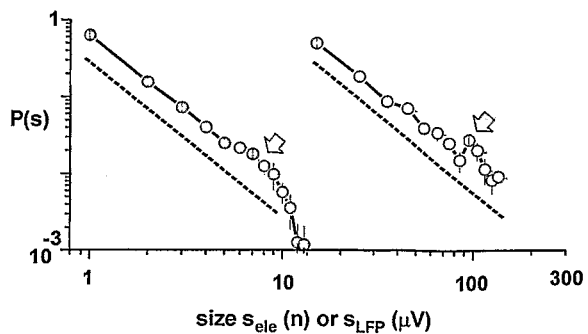

FIG. 12 illustrates neuronal avalanche recurrence depends on intact fast synaptic inhibition and differs from disinhibited spontaneous activity. A, Neuronal avalanche activity sustained by 30 μM dopamine and 3 μM NMDA ceases when the $GABA_A$-antagonist picrotoxin (PTX; 10 μM) is added. Solid line: Time course of activity in the absence of the antagonist taken from FIG. 1C for comparison. Bottom: Raster plot of nLFPs for a single, representative network. B, PTX co-applied with 3 μM SKF38393 and 3 μM NMDA prevents induction of neuronal avalanches. Numbers in brackets indicate numbers of experiments. Note difference in the y scale compared to A. C, Spontaneous disinhibited, i.e. epileptic activity induced by bath-application of PTX alone (n=6 slices) consists of relatively few nLFPs that are correlated for about 50 ms on the array (Inset: population ccf from n=6 experiments). D, Corresponding avalanche size distribution for disinhibited activity. The distributions based on $s_{ele}$ (filled circles) or $s_{LFP}$ (open circles) have an initial slope $\alpha$ close to −2 and reveal a slight increase (arrows) in the probability for large avalanches (broken lines have slope of $\alpha=-2$).

v. Neuronal Avalanches Differ from Other Types of Spontaneous Cortical Activity

The spontaneous avalanches described herein differ profoundly from other types of spontaneous activity reported in acutely isolated cortex preparations. The localization of avalanches to mainly superficial layers, their fast propagation velocity, and non-oscillatory temporal organization, all differ from the slow oscillation in cortex slices that is induced through a rise in extracellular potassium concentration. The diverse range of spatiotemporal patterns also separates neuronal avalanches from the spiral wave-like activity found in the disinhibited cortex slice. In contrast to spontaneous activity patterns reported in young mouse cortex slices, which include infragranular layers and are suppressed by low concentrations of dopamine or the $D_1$ receptor agonist SKF38393, neuronal avalanches are induced by dopamine D1-receptor stimulation. Finally, the neuronal avalanches induced by optimal dopamine-NMDA interaction are different from epileptic activity. Spontaneous activity in disinhibited neuronal network preparations are characterized by slow oscillations<0.5 Hz, which were absent in the activity induced by dopamine and NMDA. Spontaneous activity in disinhibited cortex slice cultures is characterized by a bimodal avalanche size distribution with an initial slope $\alpha<-1.5$. Similarly, in the acute slice, picrotoxin alone induced nLFPs at lower frequency, with a reduced overall duration, a slightly higher propagation speed as indicated by the reduction in $\Delta t_{avg}$, and, importantly, with a power law slope a that is smaller than −1.5 when compared to optimal NMDA-dopamine mediated stimulation. In conclusion, while an average propagation velocity of ~70 nm/s approaches the propagation speed for evoked and spontaneous activity in a disinhibited cortex slice (70-90 mm/s), neuronal avalanches represent a condition of fast propagation of activity in the presence of intact inhibition.

vi. Acute Slice Preparation and Signal Processing

Brain slices from rat 8-10 weeks old that included the mPFC were cut at a thickness of 400 μm in chilled ACSF containing (in mM) 124 NaCl, 0.3 $NaH_2PO_4$, 3.5 KCl, 1.2 $CaCl_2$, 1 $MgSO_4$, 26.2 $NaHCO_3$, 10 D-glucose, and 50 μM D,L-2-amino-5-phosphonovalerate (AP5, Sigma, St. Louis, Mo., USA) saturated with 95% $O_2$ and 5% $CO_2$ (310±5 mOsm). The slices were coronally in successive order and stored submerged for 1-2 hrs at room temperature in ACSF without AP5. For recording, slices were transferred onto planar microelectrode arrays (Multichannel Systems, Germany) and allowed to attach to the array in a mixture of 25 μl chicken plasma and bovine thrombin (1,000 NIH units/0.75 ml; Sigma) under high carbogen conditions (95% $O_2$ and 5% $CO_2$) for about 8 min, after which they were submerged in ACSF at 32.5±0.5° C. saturated with carbogen at a flow rate of 3-4 ml/min. For pharmacological tests, the glutamate receptor agonist NMDA, the dopamine $D_1$ receptor agonist (+/−)-1-phenyl-2,3,4,5-tetrahydro-(1H)-3-benzazepine-7,8-diol hydrochloride (SKF38393), the $D_1$ receptor antagonist (R(+)-7-chloro-8-hydroxy-3-methyl-1-phenyl-2,3,4,5-tetrahydro-1H-3-benzazepine hydrochloride (SCH23390), and picrotoxin (all Sigma) were freshly dissolved in ACSF and bath-applied. Dopamine was applied in combination with ascorbic acid (0.01%) to slow drug oxidation.

vii. Anatomical Reconstruction of Electrode Positions

For identifying electrode locations on the array with respect to cortical layers, comparative photographs of Nissl stained sections were matched with light microscopic pictures from the acute slice recordings after correction of shrinkage from fixation. Density plots of nLFP activity were obtained by summing nLFPs on each electrode for the duration of the recording, normalized by the most active electrode. For density distributions across cortical layers, nLFP amplitudes were summed for each electrode and normalized to maximal activity per electrode on the array. Summing up row activity resulted in a density function across cortical layers, which could range from 0 (no activity at any corresponding row electrode) to 8 (each electrode in one row with maximal activity of 100%). Each density function was expressed in absolute coordinates for cortical depth with the position of the array taken into account. Population density distributions were obtained by spatially re-sampling data from different experiments at 200 μm. Borders for cortical layers were obtained separately for each mPFC slice and averaged.

viii. Statistical Analysis

All data are presented as mean±S.E.M., if not stated otherwise. The non-parametric Kruska-Wallis H-test was used to test for significant differences in mean values at n>2 drug concentrations with the non-parametric Mann-Whitney U as a post-hoc test, if not stated otherwise. Differences between two slope values were tested by using two-tailed Student's t statistic, whereas multiple comparisons between >2 slope values were analyzed with an analysis of covariance followed by a post-hoc Tukey test. Differences in nLFP activity between layers were analyzed using ANOVA.

B. Example 2

Microelectrode array recordings of ongoing or spontaneous local field potential (LFP) activity in vivo from the primary motor cortex of two awake macaque monkeys sitting quietly in darkness were used (FIG. 13A), and in vitro from rat medial prefrontal and somatosensory cortices using both organotypic slice culture and acute slice preparations (N=6 cultures, 18 slices). The array configurations covered a range of scales, spanning ~2 $mm^2$ of cortex in vitro and 64 and 36 $mm^2$ of cortex in vivo for each of the two monkeys respectively. FIG. 13B shows a representative segment of an multielectrode array recording from one monkey where the traces at each electrode reflect the LFP activity typical for the awake state. Negative components of the LFP were extracted by peak detection using a threshold at −3 SD. These extracted negative LFPs (nLFPs) were typically composed of a single negative peak, sometimes followed by a positive component (FIG. 13C). For both monkeys, about 70-90% of the units recorded simultaneously were significantly correlated with the nLFP, supporting the idea that negative LFP peaks represent local synchronized spiking. nLFPs were then grouped based on their likelihood of belonging to a single propagated event. This grouping was done by concatenating successive time bins of width $\Delta t$ that contained at least one nLFP peak until a time bin without an nLFP peak was encountered (FIG. 13D). The appropriate choice of $\Delta t$ is the value that represents the average time taken to propagate across the average inter-electrode distance ($\Delta t_{avg}$), for which both the number of missed and inappropriate concatenations are likely to be minimized.

Figure 13:
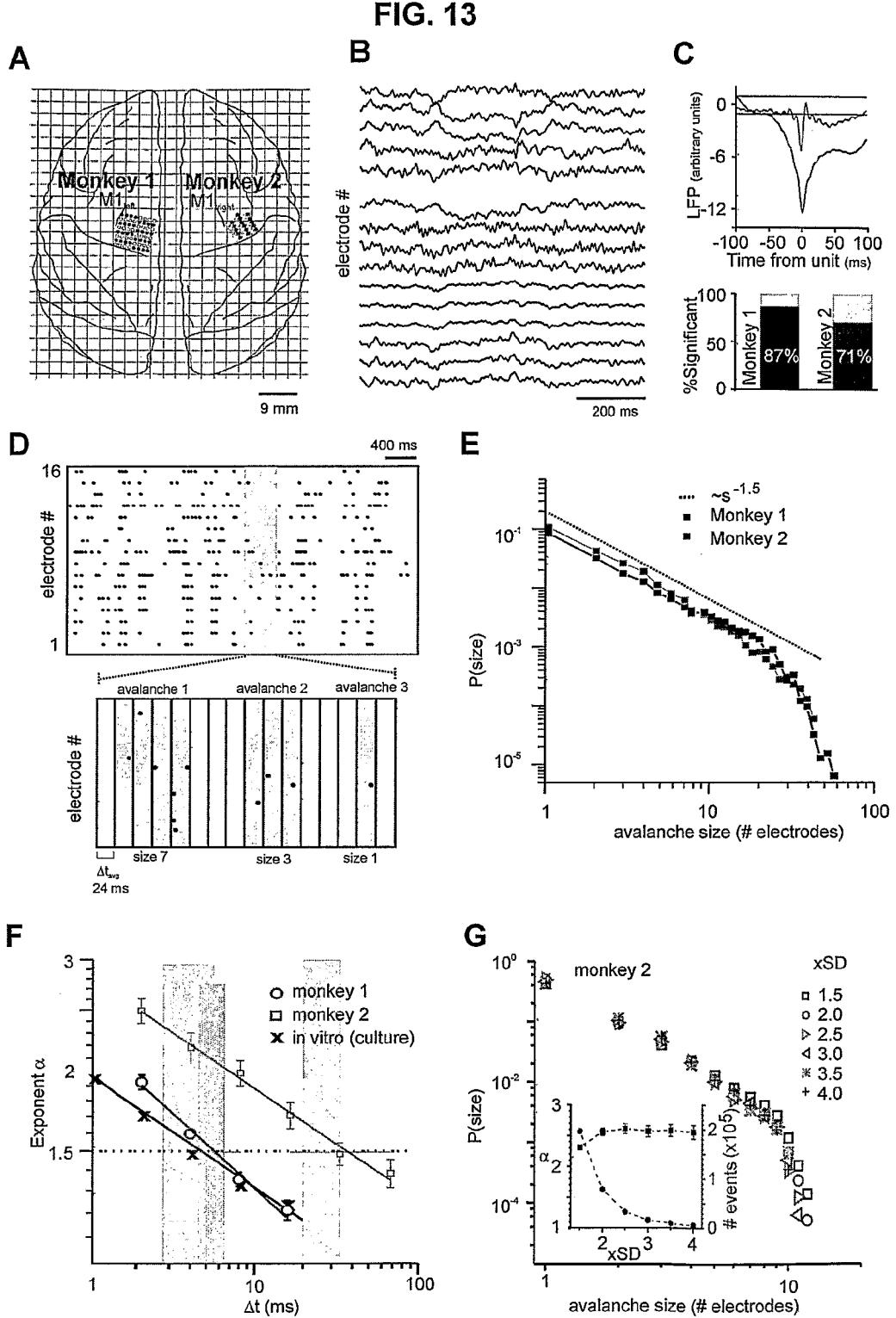
FIGS. 13 A-G illustrate that spontaneous synchronized activity in vivo organizes into neuronal avalanches.

FIG. 13 illustrates that spontaneous synchronized activity in vivo organizes into neuronal avalanches. A. Positioning of microelectrode arrays in primary motor cortex of awake monkeys (monkey 1 left, monkey 2 right). Filled circles indicate channels recorded. B. Segment of simultaneous LFP recordings in monkey 2. C. Average LFP time course within ±100 ms of the occurrence of simultaneously recorded unit activity shows a significant negative peak corresponding to unit occurrence. Black lines indicate ±99% confidence intervals. LFPs are scaled in multiples of SD. Bars indicate the percentage of units that were associated with a significant negative LFP peak (148 units in monkey 1 and 68 units in monkey 2). D. Top: Raster showing occurrence of negative LFP peaks from each of 16 channels in monkey 2 over four seconds. Bottom: expanded raster showing concatenation of nLFPs into avalanches using a bin width of $\Delta t_{avg}$ (here, 24 ms). Bins are concatenated when they are preceded and followed by at least one bin with no activity. E. Avalanche size distributions based on binning with $\Delta t_{avg}$ for both monkeys. The probability of occurrence P(size) is relatively high for small neuronal avalanches, with systematically decreasing probability for larger ones. This probability follows a power law with an exponent (slope on the log-log scale, as shown here) close to the in vitro average of ~−1.5 (shown with threshold of SD=−3 for monkey 1 and average of SD=−2 and SD=−3 for monkey 2). F. The power law behavior was preserved for any choice of $\Delta t$, as shown previously in vitro. Similarly, the exponent cc varied with $\Delta t$ as a power law according to $\alpha \propto (\Delta t)^\beta$ (relationship shown here on a log-log scale). G. The power law behavior in vivo was robust to various choices of threshold, converging to a common exponent ax for different choices of threshold in multiples of SD (inset, black) despite a significant drop in the number of peaks detected (inset, red).

$\Delta t_{avg}$ was estimated by computing the average interval between nLFP-peak occurrences over the range of intervals that were correlated between electrodes (see formula 1-3). $\Delta t_{avg}$ differed somewhat between networks giving rise to mean velocities between 30 and 70 mm/s in all in vitro networks and in vivo in monkey 2. This range was similar to other measurements of propagation velocities in cortical tissue in vivo and in vitro. Monkey 1 however, differed from monkey 2 in having a mean velocity of 200 mm/s. The faster speed may relate to the presence of a strong oscillation in monkey 1. Some oscillations have been shown to propagate at more rapid velocities of 200-500 mm/s.

When nLFPs from awake-monkey recordings were grouped as described above, they carried the spatiotemporal signature of the 'neuronal avalanches' that have been described previously in acute slice and organotypic culture from cortex. First, at a bin width of $\Delta t_{avg}$, the spatial size of these groups (i.e., the number of electrodes engaged) distributed according to a power law with an exponent, $\alpha$, close to the in vitro average of −1.5 (−1.4 in monkey 1, −1.65 in monkey 2; FIG. 13E). Second, the power law was preserved for different choices of $\Delta t$ (FIG. 13F). Third, its exponent $\alpha$ scaled with $\Delta t$ as a power law, $\alpha \propto (\Delta t)^\beta$ ($\beta$=0.16±0.01 in vitro, 0.23±0.02 monkey 1, 17±0.01 monkey 2). As a further demonstration of the robustness of this phenomenon in vivo (FIG. 13G) this behavior was insensitive to the choice of threshold despite a progressive and significant decrease in the number of peak detections (≥2 SD from the mean; shown here at $\Delta t$=2 ms, the resolution of the in vivo recordings).

The emergence of the power law distribution indicates an important principle of the organization of synchronized activity in the cortex, namely the existence of long-range spatiotemporal correlations that allows the formation of a large diversity of pattern sizes in a 'scale invariant' manner. If nLFPs were randomly organized in space and time, the grouping would result in a simple exponentially decaying size distribution, where the occurrence of large groups would be extremely rare. The dynamics are also distinct from epileptiform activity studied in disinhibited slices[23], which is characterized by a preponderance of large groups and thus lacks the diversity of group sizes demonstrated by the power law.

Each neuronal avalanche represents a naturally occurring spatiotemporal pattern of local synchrony. This allowed the study of how successive activation of synchrony at various spatial locations takes place in the cortex in the context of pattern formation. The properties of nLFP propagation within an avalanche were examined on a millisecond time scale (1 ms in vitro and 2 ms in vivo, the temporal resolution of the recordings). For this analysis it was assumed that, in the aggregate, the temporal order of detected nLFP peaks approximates the temporal path of the avalanche.

Provided is a precise analysis and demonstration that the branching parameter sigma is log(mode)=0 in vitro and in vivo in the critical state, i.e. when $\alpha$=−1.5. The propagation of LFPs was analysed for systematic decay or explosion within an avalanche. For this purpose, nLFP areas were calculated by integrating the LFP from the first crossing of the baseline before the peak (peak≥3 SD) to the first crossing after the peak. The nLFP areas measured in each network spanned a≥4 fold range in all cases, although each in vivo network had different ranges owing to different signal to noise characteristics (FIG. 4A). To study the progressive changes in event size within an avalanche, the area of the nLFPs with peaks that occurred in each subsequent time bin was normalized to the area of the first nLFP in that same avalanche. To linearize the distribution of ratios, distributions were plotted on a $\log_2$ scale. As shown in the representative cultured slice, acute slice and in vivo networks in FIG. 4B, the distributions of these normalized values yielded similar symmetric distributions centered at 0 ($\log_2(1)$) for up to 20 successive time steps demonstrating the absence of a progressive spatial dissipation, decay or growth of activity.

The average of the modes of these distributions for all cultured (left) and acute (middle) slice networks and the modes for each individual in vivo network (right) are shown in FIG. 4C, indicating that the initial event size tends to be preserved at all steps. It was then determined whether this could have occurred by chance, by asking what random ordered pairings of nLFPs from different electrodes would look like. Specifically, the rarely occurring large events were focused on, which represented only 10% of the total nLFP pool in each network (i.e. ≥$90_{th}$ percentile in nLFP area). For these events, the expected distribution from random pairings was significantly left-shifted, reflecting the high probability of subsequently drawing a small event. In contrast, the distribution obtained from within avalanches showed a dominant peak at 0 (i.e. $\log_2 1$) in each culture, acute slice and in vivo network ($p<10_{-10}$ by Kolmogorov-Smirnov (K-S) test for all networks).

FIG. 4 nLFPs within an avalanche maintain the initial event size, i.e. reveal a branching parameter of log(mode)=0. A. Cumulative distribution of all nLFP areas for cultured (left) and acute (middle) slices and in vivo (right). Areas spanned a wide range (~8 fold culture (right), ~3 fold slice, >5 fold in vivo) but tended to cluster at the lower values. Insets: nLFPs of varying areas within the range indicated by the arrows. B. Distributions (from representative networks) of nLFP areas at each successive time step normalized to the 1st nLFP and linearized on a log 2 scale. Data show a 0-centered symmetric distribution that is preserved at all steps. C. The mode of the distributions shown in B for all cultured and acute slice networks (mean±SEM) and each of two in vivo networks shows the tendency for constant event size over all time steps in an avalanche. D. Normalized area distributions (as in B) restricted to rarely occurring avalanches with large initial LFPs (areas ≥90th percentile) had a dominant peak at 0, significantly different from the distribution obtained from random ordered pairings (gray) ($p<10$-10 by K-S test).

Figure 14:
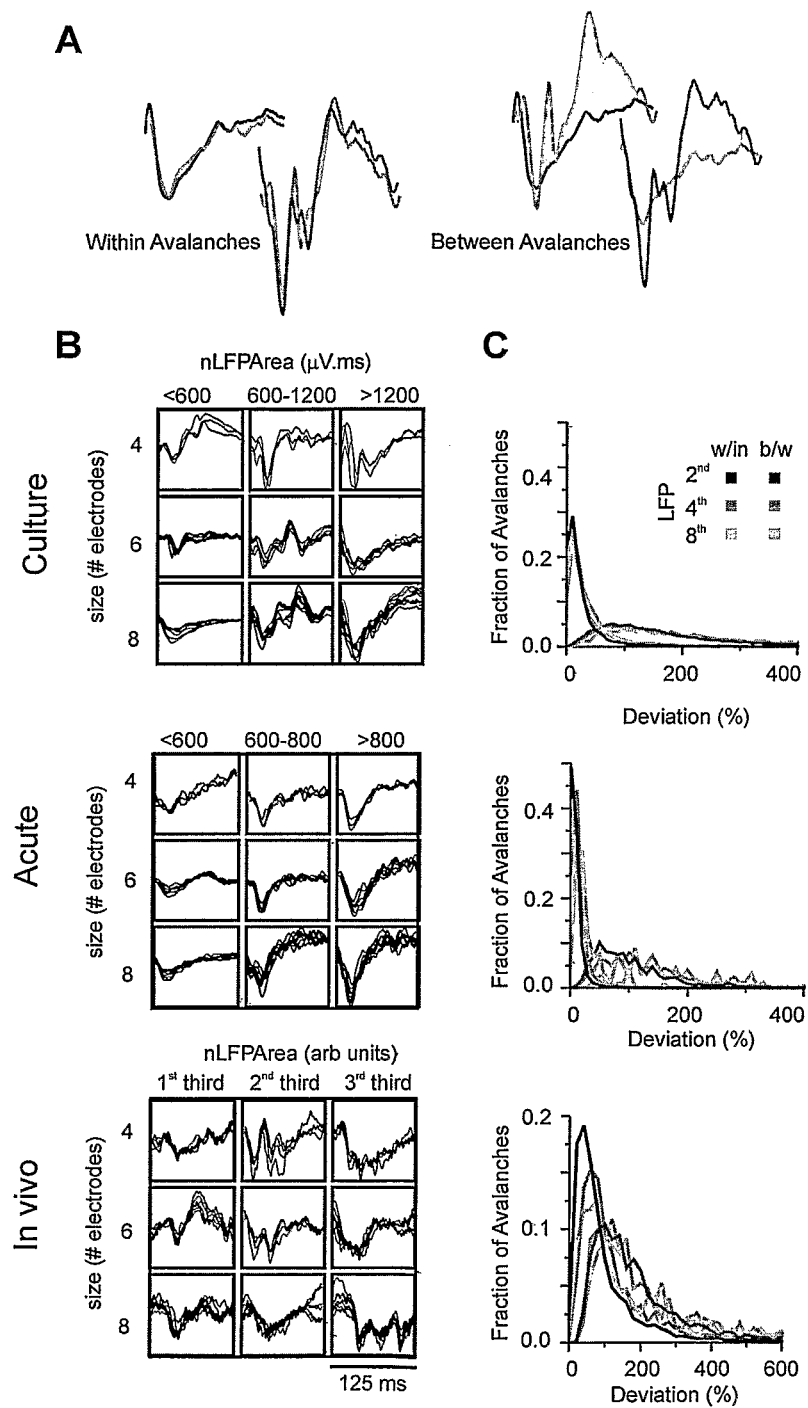
FIGS. 14 A-C illustrate nLFPs within an avalanche maintain the waveform of the initial event.

This finding prompted the question of whether there was a more precise preservation of nLFP waveform, perhaps reflecting a precise spatiotemporal pattern of synchronized activity within the local field. Indeed, overlays of nLFPs within an avalanche (examples in FIG. 14B), demonstrated a similar pattern at each participating electrode for avalanches composed of nLFPs of all sizes and spanning varying numbers of electrodes. This would not be surprising if the nLFP waveforms were homogeneous overall. Thus, as a rigorous test of this similarity, the total deviations in the waveform between the $1^{st}$ nLFP and the $n_{th}$ nLFP were compared (n=2, 4 and 8) within an avalanche and between avalanches (Σ shaded area, FIG. 14A) as a percentage of the area of the $1_{st}$ nLFP. To exclude differences arising due to differences in the area of nLFPs, avalanches were binned according to the area of the initial nLFP in an avalanche, and the between-avalanche comparisons were made for area-matched nLFPs in each bin. FIG. 14C shows distributions constructed by pooling the deviations from all the area-binned comparisons. In both cultured and acute slices, the mean within-avalanche deviations were ~8-fold smaller than the between avalanche deviations for area matched comparisons ($p<0.0001$ by t-test for mean difference in each area bin, $p<10_{-100}$ by K-S test for the difference between distributions shown in FIG. 14C). In vivo, the mean difference was ~2.5 fold ($p<0.01$ each area bin by t-test; $p<10_{-10}$ by K-S test for the difference between distributions shown in FIG. 14C, both networks).

This difference was far lower than in the in vitro preparations, owing perhaps to the greater distances separating electrodes, the higher rate of activity overall, and interactions with distant brain regions, all of which would lead to a higher incidence of misgrouping of propagated events. Within an avalanche, deviations increased slightly for nLFPs occurring further in time from the first event (culture: $p<0.001$, $n>1000$, acute slice: $p<0.01$, $n>100$, in vivo $p<10$, $n>500$ between $2_{nd}$ and $8_{th}$ nLFP comparisons by K-S test), but were in all cases many-fold smaller from their corresponding between avalanche comparisons. This large difference indicates that despite the large diversity of waveforms, the cortical network is capable of maintaining a precise memory of a waveform as it propagates, perhaps indicative of the preservation of a particular spatiotemporal sequence of synchronized spikes.

Figure 15:
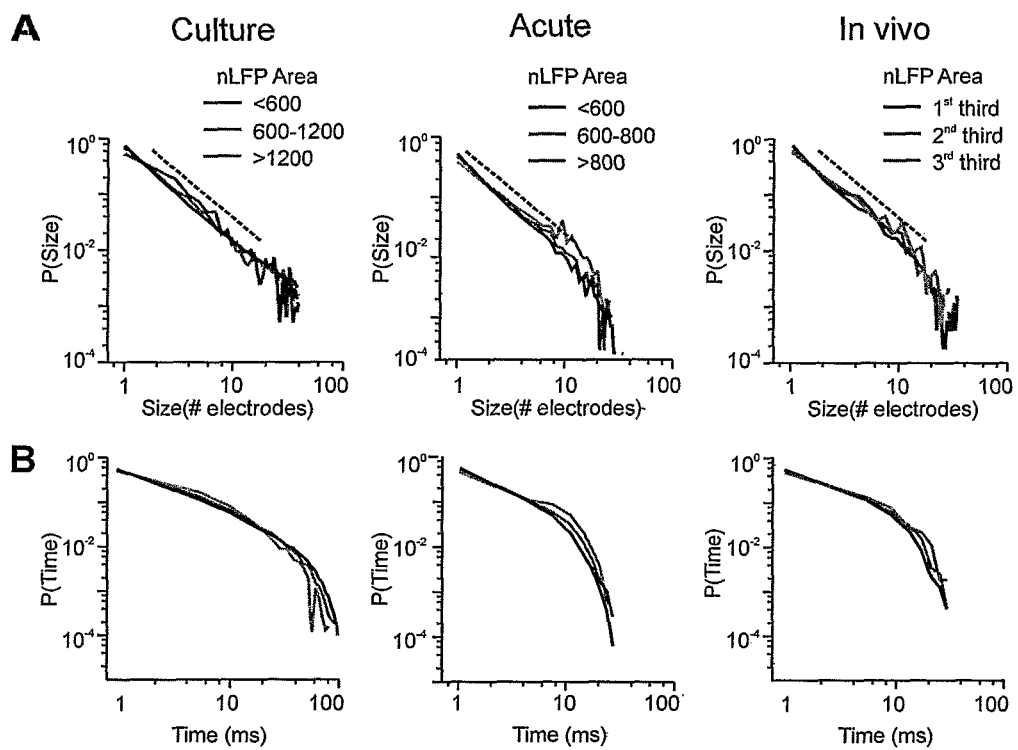
FIGS. 15. A-B illustrate spatial and temporal influence of avalanches are independent of initiating LFP area.

It was then determined how the size of the initiating event affected the spatial extent of an avalanche (as measured by the number of electrodes engaged; FIG. 15A). One could imagine a scenario in which avalanches with smaller initial nLFPs would tend to die out faster without propagating far, as shown in models of synfire chains, whereas those with large initiating nLFPs (presumably representing many more synchronized spikes within the same local field) would tend to display greater spatial spreads across the cortex. To test this hypothesis, avalanches were divided into three groups based on the initial nLFP area and compared the dynamics of each of these groups. It was found that there was no significant difference in the distributions of avalanche sizes (i.e., the number of electrodes engaged) between any of the groups for each network ($p>0.5$ for difference between these slopes on log-log scale). Both in vivo and in vitro, the size distributions followed a power law with slope ~−1.5, similar to the overall distribution that has been previously described is. Similarly, when one compared the time taken for all participating electrodes in an avalanche to become engaged (i.e., the interval between the first and last peaks), once again there was no difference between any of these groups ($p>0.5$, culture; $p>0.2$, slice; $p>0.2$ in vivo for all comparisons by K-S test) (FIG. 15B). Thus small groups and large groups were equally capable of rapidly engaging groups across long distances.

The balance of excitation and inhibition is crucial for cortical function and is maintained under different levels of activity. Inhibition can synchronize activity and control the probability and temporal precision of spikes. Therefore the role of inhibition in maintaining the features of neuronal avalanches that described herein was tested. To do so, the cultured networks were used, which allowed for stable recordings over long periods under controlled conditions.

Figure 16:
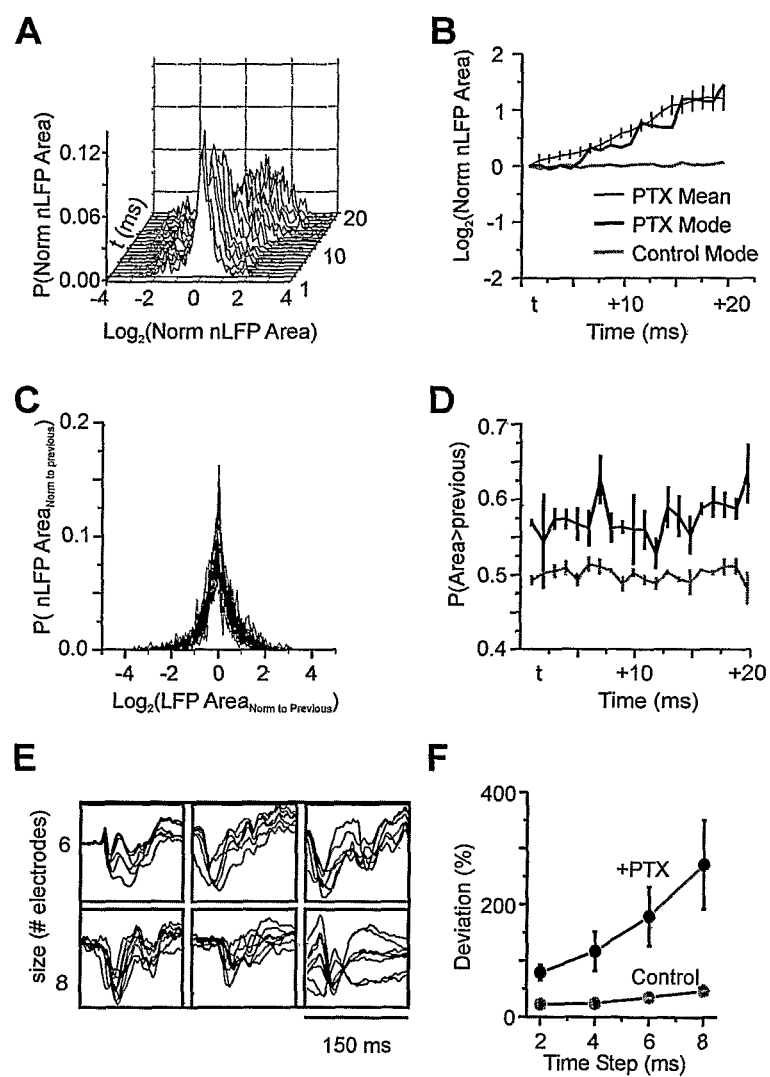
FIGS. 16 A-F illustrate $GABA_A$ inhibition maintains the fidelity of transmission of synchrony.

An experimental demonstration is provided that in the epileptic, i.e. disinhibited state, the branching parameter sigma follows log(mod)>0. In the presence of a low concentration (5 μM) of the $GABA_A$ antagonist picrotoxin (PTX; N=4 cultures), the average rate of spontaneous nLFPs decreased by 80±23%. Within avalanches, there was a consistent trend towards larger nLFPs relative to the initial nLFP as demonstrated by the increasingly right-skewed distribution in FIG. 16A. In contrast to control cultures, both the mode and mean of these distributions increased with each successive time step (FIG. 16B). Whereas under normal conditions, the likelihood to be larger than the nLFP in the immediately preceding time step ($P(\log_2(Area)_{Norm\ to\ previous}>0)$) was exactly 0.5; when inhibition was reduced, i.e. under epileptic conditions, there was a significant and consistent increase in this probability, to ~0.58, at every time step considered (FIGS. 16C,D). An even more profound effect of reduced inhibition was evident in the precision with which nLFP waveforms were maintained. The application of PTX increased the deviations in nLFP waveforms relative to the initial nLFP by ~3.5-fold in the first time step alone, an increase that grew to ~6-fold within 8 time steps ($p<0.0001$; FIGS. 16E,F). These deviations were clearly visible in the larger variety of waveforms within any avalanche (FIG. 16E, cf FIG. 14B). The active preservation of waveform by fast inhibition argues against the suggestion that similar waveforms measured at different electrodes reflect either activity from the same local neuronal group or a stationary synchronization across the network. In fact, it argues strongly for the propagation of synchronized activity, which under normal conditions obeys the rule of σ=1, or log(mode)=0.

These findings identify three active roles for fast $GABA_A$ mediated inhibition at the network level that could not have been predicted by single-cell studies: (1) spontaneously generating local synchronized activity, i.e., nLFPs, (2) maintaining a balance between the probability of increasing or decreasing in size during propagation, and (3) preserving the temporal characteristics of the initial local event during propagation of synchrony.

In summary, evidence has been provided that the organization of spontaneous synchronous activity into neuronal avalanches is a robust feature of cortex that is present in vivo in the awake state and in in vitro preparations where key aspects of the cortical architecture, such as cortical layers, are preserved.

Neuronal avalanches are diverse spatiotemporal patterns whose sizes are distributed according to a power law. This indicates that avalanches occur at all spatial scales, a property that is further reflected in the robustness of this organization to the number of electrodes and interelectrode distance used. Avalanches spanned a maximal cortical distance of up to 1.7 mm in vitro and 11.2 mm in vivo, a spatial extent that reaches well beyond a single cortical column$_{27}$. Remarkably, within an avalanche, synchrony translated with high fidelity in space, i.e., preserving the precise waveform at different locations, before it disappeared abruptly. This feature was highly dependent on fast inhibition.

Smaller nLFPs were equally likely to propagate over long cortical distances as large ones. This demonstrates that the cortex robustly supports the lossless propagation of synchrony not just without spatial dissipation, decay or explosion but also without destroying its precise temporal properties.

It is now well established that the coherent spatiotemporal structure of spontaneous activity reflects the rich functional organization of the cortical network and profoundly affects cortical input processing. Importantly, spontaneous transient synchronizations at multiple cortical sites, when preceding behaviorally relevant periods, significantly increase network responses and improve behavioral outcome, e.g. reaction times. This improvement in network performance is thought to result from the spontaneous grouping of synchronized neurons into cell assemblies, thereby selectively increasing responsiveness of target neurons involved in stimulus processing. Theory has suggested stable and selective propagation of synchrony as a solution to the formation of these cell assemblies in the cortex. Similarly, the transient synchronizations observed in LFPs and EEGs have been previously analyzed in the framework of 'phase synchronization', whereby synchrony transiently occurs at multiple sites in a phase-locked manner with precise time lags, but not necessarily preservation of waveforms, suggesting a role for this 'phase synchronization' in cognitive function. The findings presented here provide new insights into how synchronized activity manifests in cortex and new guidance for the theoretical and experimental exploration of cell assemblies using synchrony. On the one hand, the successive induction of distant, synchronized events is constrained by the preservation of the properties of the local synchronized event, in this case its waveform, indicating not only a precise transient phase locking with time lags corresponding to fast propagation but also a preservation of all other parameters such as amplitude and total charge. On the other hand, the event is conferred with many degrees of freedom by virtue of the independence of propagation success, as measured by the spatial distance spanned, from the properties of the waveform. Significantly, this lossless transmission creates a memory of these properties during the propagation process that extends over several tens of milliseconds. This process of transmission binds distant regions of the cortex, both temporally and by virtue of common features, suggesting an important role in information transmission and associative processing of the neocortex.

Organotypic cultures from slices of rat cortex were prepared in accordance with NIH guidelines. Coronal sections from rat brains (Sprague Dawley, Taconic Farms, Md., USA) at postnatal day 0-2 were cut at 350 μm thickness. A coronal slice section containing dorsal or dorsolateral cortex (~1.5 mm deep and ~2-3 mm wide) was positioned on a multielectrode array (Multichannelsystems, Reutlingen, Germany). The array covered ~50-70% of the cortical tissue with the bottom row aligned to infragranular layers and the upper rows extending beyond layer I. This arrangement allowed for the dorsal expansion of the cortical slice on the multielectrode array, which results from the development of superficial layers during the first weeks postnatal in rat cortex. The slices were attached to the pre-cleaned, poly-D-lysine coated multielectrode array-surface by coagulation with 15 μl chicken plasma and 15 μl of bovine thrombin (Sigma St. Louis, Mo., USA), after which cultures were grown at 35.5° C. in normal atmosphere in a culture medium consisting of 50% Basal Medium Eagle, 25% Hanks Balanced Salt Solution and 25% horse serum, 0.5% glucose, and 0.5 mM L-glutamine (all Gibco, Grand Island, N.Y., USA). Photographs taken at 1-3 DIV and after recording sessions confirmed the position of recording electrodes in the cortical tissue and organotypic cortex slice culture.

A custom-built incubator was used in order to allow for long-term pharmacological experiments and repetitive, sterile recording sessions at different developmental stages under identical recording and culturing conditions. The chamber design and preparation of the multielectrode array for recordings has been described in more detail previously. In short, each multielectrode array consisted of a square glass plate (5×5 cm, 1 mm thickness) with a square array of 60 microelectrodes made of titanium nitride (8×8 grid with the corners missing) at its center (Egert et al., 1998). Titanium nitride electrodes were flat and disk-shaped with a diameter of 30 μm, an inter electrode spacing of 200 μm, and were attached to gold leads that ended at the edge of the glass square and served as contacts for the amplifier head stage. A circular glass well (~10 mm diameter) with a Teflon cap was centered and cured to the glass plate by Sylgard® functioned as a tight-sealed, sterile culture chamber.

Multielectrode arrays were placed onto storage trays inside the incubator and gently rocked. The temperature inside incubator was maintained at 35±0.5° C. For optimal culture survival and culture growth a rocking trajectory was used that approximated a sinusoidal function (~400 s cycle time) with brief halts of ~10 s at the steepest angle before reversing directions. At the points of direction reversal, cultures were exposed to the inner chamber atmosphere. Through this arrangement, the culture medium was in constant motion, which resulted in superior growth of cultures for up to 2 months. After 3 and 27 days in vitro (DIV), 10 ml of mitosis inhibitor was added for 24 hr (4.4 mM cytosine-5-b-arabinofuranosid, 4.4 mM uridine and 4.4 mM 5-fluorodeoxyuridine; calculated to final concentration; all Sigma). Medium was changed every 3-5 days. No antibiotics were used throughout cultivation and recording periods.

For recordings, individual multielectrode arrays were placed into the recording head stage (MultiChannelSystems, Inc.), which was affixed to a second tray within the incubator and had the exact same motion as the primary storage tray. This allowed recording in culture medium under conditions identical to growth conditions. The exchange between recording and storage location for each multielectrode array took few seconds and was done without interruption of the rocking cycle. Activity occurred spontaneously in organotypic cortex cultures and was recorded up to 5 hrs giving rise to >10,000 avalanches per network.

Acute mPFC slices from adult rats were prepared as described (see above). Activity in acute slices was elicited by bath application of a combination of 3 μM N-Methyl-D-Aspartate(NMDA) and 3 μM of the dopamine D1-receptor agonist (+/−)-1-phenyl-2,3,4,5-tetrahydro-(1H)-3-benzazepine-7,8-diol hydrochloride (SKF38393) and persisted up to 1 hr giving rise to >1000 avalanches per network.

Overall, negative local field potentials (nLFPs) occurred at 82±5% of the electrodes in the acute slices and 88±5% of the electrodes in cultures. Data was sampled at 1 kHz and low pass filtered at 50 Hz. To look at the effects of inhibition, 5 μM picrotoxin was added directly into the medium of the cultures after 2 to 5 hours of baseline recording and recordings were continued for 2 to 5 hours.

In vivo recordings were carried out in two awake adult macaque monkeys sitting quietly in a dark room and chronically implanted with arrays of 30 mm diameter monopolar tungsten electrodes (1 MΩ impedance) that were 1.5 mm in length. LFP and unit activity was recorded simultaneously from 16 electrodes in monkey 1 and 32 electrodes in monkey 2 placed 1 mm and 2 mm apart along the two axes (filled circles, FIG. 13A). Recordings were for 43 minutes in monkey 1 giving rise to ~6,000 avalanches and 47 minutes in monkey 2 giving rise to ~5,000 avalanches. Data was sampled at 0.5 kHz and band pass filtered between 1 and 100 Hz for LFP analysis. At some electrodes, a large peak was observed in the power spectrum at the AC frequency of 60 Hz which was removed by filtering out the band corresponding to 60±0.05 Hz. Negative local field potentials (nLFPs) were detected at all electrodes in both monkeys. Units were extracted using the spike sorting algorithm developed by Plexon (Plexon Inc, www.plexoninc.com)

In the in vitro networks, LFPs whose negative peaks were below −3 SD of the noise histogram were extracted at each electrode for further analysis. In vivo, due to the absence of a clear baseline or noise fluctuations, the detection threshold for negative LFP peaks at each electrode was determined as −3 SD of the overall activity profile after excluding segments that exhibited high, amplitude, slow-wave activity. These excluded slow-wave segments were defined as having 90% of the power between 1 and 10 Hz and were identified by calculating the power spectra within a sliding window of 2 s duration at successive time intervals of 1.5 s. Segments of the recordings where this slow-wave activity was present on >50% of the channels were excluded from all subsequent analysis (~5-10% of the recorded data).

To check to what extent unit activity corresponded to negative LFP peaks, the portions of the LFPs within ±100 ms of unit occurrences were averaged. The same procedure was performed for a randomized time series of unit activity. The confidence interval for negative peak significance was taken to be 2.58 SD (p>0.99) of the distribution of LFPs around the time-randomized units. LFPs with negative peaks beyond the confidence interval were considered significant. To assess to what extent negative LFP peaks correlated with unit activity the distribution of unit occurrences within ±100 ms of the negative LFP peaks was calculated. Two additional arrays placed in the premotor cortex were used for monkey 2 for this analysis.

In each network, both in vivo and in vitro, cross correlations between nLFP peak occurrences were calculated between each electrode pair as previously described. The average cross correlation across all pairs was then used to determine an inter-event interval (IEI) cut-off by visually selecting a range of values where the cross correlation had decayed close to zero. In the case of monkey 1, due to the presence of an oscillation, the cut-off was chosen as the first minimum. $\Delta t_{avg}$ was then calculated as the average IEI interval for those values below the cut-off. This calculation yielded values of 3.0±0.2 ms for the acute slices, 5.8±0.2 ms for cultures and 5.5±1.0 ms and 26.8±6.9 ms for each of monkeys 1 and 2 respectively. These average values were then rounded to the nearest integer for the in vitro networks and to the nearest multiple of 2 for the in vivo networks (since the data was acquired at 1 and 2 ms resolution respectively).

Within avalanches, nLFPs were compared at the recorded 1 ms or 2 ma resolution. nLFP order within avalanches, calculated by both start time and peak time, were compared and found to be >80% similar. Peak time was considered more accurate due to the better resolution beyond the noise and used to determine temporal order. To calculate deviations in the waveforms of nLFPs, nLFPs were peak aligned and the deviations calculated between the first start and last end of the negative deflections. All analyses of deviations in area and waveform were carried out within avalanches where there was only one nLFP peak in the first millisecond time bin.

Between-avalanche comparisons were made by first grouping avalanches by the area of the 1st nLFP and then shifting the nth nLFPs in these groups of avalanches by 5 places; i.e. the 1st nLFP of avalanche i was compared to the nth nLFP of avalanche i+5. This was repeated for various shifts with no difference. Area-wise binning restricted differences attributed to area in the between avalanche comparison to a maximum of 5%. For comparisons of size distributions and peak-to-peak times of different LFP sizes, size classes were defined based on three equally sized groups (i.e. 1st third of nLFPs, 2nd third of nLFPs and 3rd third of nLFPs). While this did not yield an equal spacing of size, it provided an equal number of data points in each group for better distribution statistics.

C. Example 3

Oscillatory

The NAS assay can be constructed based on oscillatory activity, i.e. gamma oscillations measured from superficial cortical layers. This allows the use of an Electroencephalogram (EEG) as a neuronal activity detector. Gamma-oscillations are readily revealed in EEG measurements.

Synchronized neuronal activity at millisecond precision such as γ-oscillations is considered to be important for higher cortical functions such as feature binding, selective attention, and consciousness. γ-band oscillations are found early on during development, e.g. as human infants develop feature-binding capabilities, and their beneficial roles are clearly demonstrated in adults, where γ-frequency power is positively correlated with the difficulty level during working memory tasks. On the other hand, an increase in γ-synchrony has been associated with positive and a decrease with negative symptoms of schizophrenia raising the question whether there is an optimal regime in which γ-oscillations occur in the cortex and how this regime is regulated. Disclosed herein is a previously unrecognized relationship between γ-oscillations and neuronal avalanches that can be used to determine the optimally balanced network state capable to support γ-oscillations.

γ-oscillations allow for the fast synchronization of neuronal activities over long distances with millisecond precision. Such synchronization can be beneficial under certain circumstances, e.g. linking distant cortical sites for feature findings, however, too much synchronization can lock the cortical network into a redundant dynamic, which would be detrimental for information processing. Neuronal avalanches that distribute in sizes according to a power law with α−3/2, were originally described as a non-oscillatory mode of synchronization that occurs at the millisecond level. The fast propagation of synchrony over long cortical distances are features that neuronal avalanches share with γ-oscillations. Furthermore, neuronal avalanches, which often last no longer than 20 ms, fit into a single γ-oscillation cycle. Evidence is provided for the co-existence between γ-oscillations and avalanches. An optimization function is derived for neuronal avalanches in oscillatory networks, which in turn allows for the understanding of optimal γ-oscillations formation in cortical networks.

In order to develop an experimental paradigm to study the relationship between γ-oscillations and neuronal avalanches, the time of development of superficial cortical layers was focused upon. First, γ-oscillations as well as neuronal avalanches originate in superficial cortical layers. Second, dopamine plays a neurotrophic as well as acute role in regulating both dynamics. γ-oscillations and neuronal avalanches require fast GABAA-mediated synaptic inhibition and dopamine provides neurotrophic action to interneurons in superficial cortical layers, whereas the acute induction of neuronal avalanches depend critically on the dopamine D1-receptor. Therefore an immature cortex slice was cultured at postnatal day 2 with a section of the midbrain, which contains the ventral-tegmental area (VTA). In this co-culture, superficial cortical layers will develop during the second week postnatal in vitro in line with the time course of postnatal development in vivo. Around this time during development, the VTA establishes dopaminergic inputs to the cortical network.

This in vitro system gave rise to spontaneous γ-oscillations that were organized into neuronal avalanches. The avalanche size distribution revealed a power law slope of $\alpha=-1.5$. This optimized propagation of synchrony during γ-oscillations in superficial cortical layers was maintained through balanced dopamine $D_1/D_2$ receptor activation intrinsic to superficial layers and was critically dependent on GABAA-mediated synaptic transmission (FIG. 17-23).

Cortical extracellular neuronal activity was recorded in organotypic cortex-VTA cultures using 8×8 multielectrode arrays (FIG. 17A). The activity in the cortical tissue started as isolated single unit activity, which later formed bursts of multi-unit activity in the form of oscillations (FIG. 17B). Within the first 9±2 days in vitro (DIV; mean=8.33 days, range 7-11 days, n=9 networks) cultures showed strong oscillatory field potentials, which activity persisted up to 16-22 DIV. The appearance of oscillatory activity ranged from closely placed isolated LFPs to frank sinusoidal waves lasting from 50 ms to 500 ms. The amplitude of activity in cycles showed an initially increasing and then decreasing trend with maximal amplitudes during the middle period the oscillatory burst. LFP amplitudes varied from −10 μV to −1200 μV (mean=−38.2±3.4 μV) and varied between cultures −10.68±0.53 μV to −223.6±19.25 μV (mean high value).

Frequency domain analysis of LFP waveforms revealed that activity periods contained two main frequency bands (FIGS. 17C,D). The lower frequency component had a peak in the range of 2-16 Hz (mean=7.5±1.4 Hz) and the higher component had a peak ranging from 40 to 105 Hz (mean=77±8.8 Hz). Power in the waveforms revealed significant difference between the mean power values in the noise and oscillations in the γ-range frequencies (e.g. noise: 1.0003±0.94 μV², signal: 118.48±38.41 μV², p=0.01).

Figure 17:
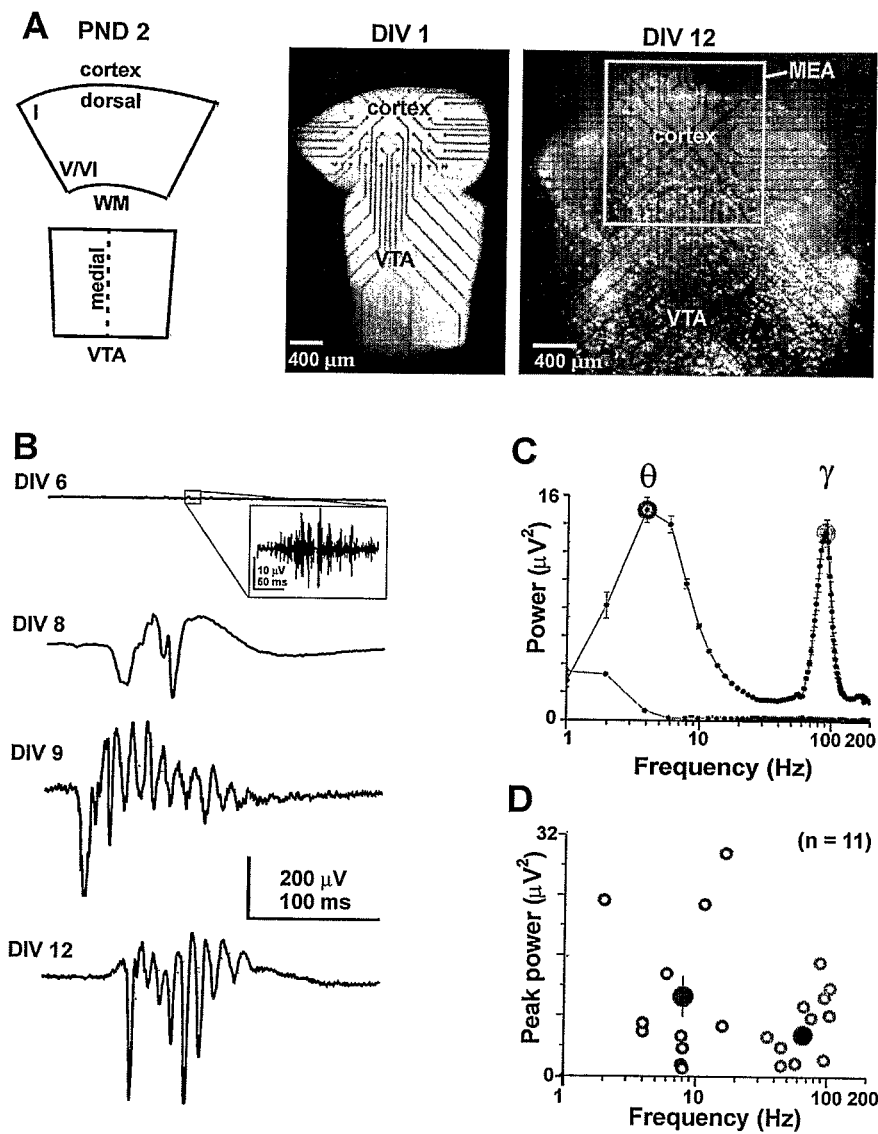
FIGS. 17 A-D illustrate spontaneous LFP bursts composed of $\delta/\theta$ and $\gamma$-frequency oscillations occur at the time of superficial layer differentiation in cortex in vitro.

FIG. 17 illustrates spontaneous LFP bursts composed of δ/θ and γ-frequency oscillations occur at the time of superficial layer, differentiation in cortex in vitro. A. Development of the organotypic cortex-ventral tegmental area (VTA) culture on the multielectrode array. Left: Position and orientation of the acute coronal cortex and VTA slice for culturing (WM: White mater; I, V/VI: layers I and V/V respectively). Light microscopic picture of a co-culture at 1 day in vitro (DIV; middle) and at 12 DIV (right). The position of the cortical slice on the multielectrode array (open square) allowed for LFP recordings from 60 sites across and as well as along cortical layers. B. Spontaneous bursts of oscillatory LFPs emerge at around 8 DIV and persist throughout the second week of, culturing, i.e. ~8-16 days postnatal. Single LFP bursts at different times of development (same culture). Spontaneous activity before LFP oscillations is characterized by clustered multi-unit activity (inset at DIV6). C. Bursts are composed of a θ- and γ-oscillation at 4 Hz and 80 Hz respectively (Average power spectrum from in a single network; mean±SD). Red line: Corresponding power spectrum from extracellular activity before burst onset, i.e. noise. D. Summary plot of peak amplitudes vs. peak δ/θ and γ-frequencies (n=11 cultures).

Organotypic co-cultures were prepared from the frontal cortex (EC) and ventral-tegmental area (VTA) isolated from postnatal day 1-2 (PND) old rats. The VTA slices were cut at a thickness of 500 μm and cortex at 350 μm. The culture was done with cortex placed on multielectrode arrays (Multichannel Systems, Reutlingen, Germany) with electrode diameter of 30 μm and interelectrode distance of 200 μm. Cultivation and recording was done in a sterile chamber on the microelectrode array as described above. The culture was kept within the incubator with the rocking movement (~0.005 Hz) throughout the recording. Spontaneous extracellular signals were recorded at a sampling frequency of 4 kHz with 1 kHz low pass filtering continuously for an average of 4±1 hrs. The temperature inside incubator was maintained at 35±0.5° C.

Neuronal oscillatory activity was analyzed by calculating the power spectrum from periods of prominent LFP activity, i.e. LFP bursts using a discrete Fast Fourier Transform in Matlab (Mathworks). Periods of prominent LFP activity were identified by negative threshold crossing at −3 SD from electrode noise. When calculating the average power spectrum for an activity period on the array, the duration for selecting activity periods was taken as the average duration of individual oscillatory activity in each recording session. While taking activity regions care was taken to avoid recalculation of spectra from the same time period in same electrode. The power spectrum of noise for each electrode was separately calculated from 20 separate recording regions where no activity was present and the power in the noise was subtracted from that in the signal. The selected signal region was filtered with a Hanning window (a cosine window defined by: $w(k+1)=0.5*(1-\cos(2*pi*(k/(n-1))))$, k=0, 1, 2 ... n−1) before calculating the power spectrum. The power spectrum of each activity period was calculated and averaged from all the active electrodes in each activity period. Then the power spectrum was averaged over the entire 4 hr recording.

Experimental evidence is provided that the cortical δ/θ and γ-frequencies in the in vitro co-culture system are also dominant in superficial cortical layers, which is similar to the location found for neuronal avalanches in adult rat cortex. To locate the origin of oscillatory activity within the layered cortical cultures, a two dimensional current source density (CSD) method was employed. Only networks where the multielectrode array covered the complete extent of the cortical culture, i.e. across all layers, were used for this analysis (FIGS. 18A,B; n=10 cultures). CSD revealed that current sinks, which are indicative of synchronized inward currents, e.g. synaptic inputs and action potentials, were strongest in superficial cortical layers. The mean sink strength was at 200 μm from the dorsal border of the cortex was −1.34±0.5 μV/μm² compared to that of −0.05±0.23 μV/μm² at 600 μm distance (FIGS. 18B,D). During a burst, sinks and sources alternated within superficial layers with gamma oscillation cycles (FIGS. 18A,C).

Figure 18:
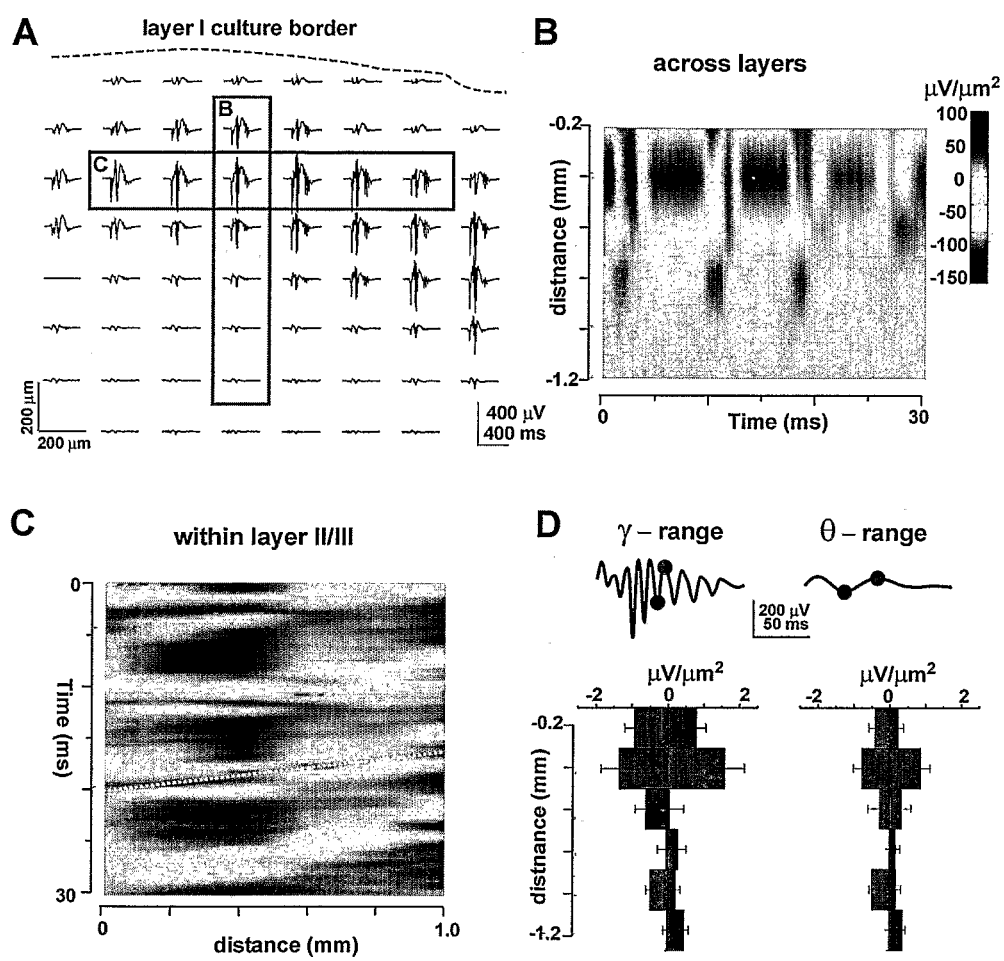
FIGS. 18 A-D show that $\gamma$-oscillations reflect propagated waves within superficial cortical layers.

FIG. 18 shows that γ-oscillations reflect propagated waves within superficial cortical layers. A. Simultaneous recording of oscillatory LFPs during one burst period (8×8 electrode configuration at 200 μm interelectrode distance). B. γ-oscillations are located in superficial cortical layers II/III (~100-300 μm distance from the upper cortical border). 2-D CSD along the depth of the cortical culture reveals prominent sinks alternating with sources for 3 γ-cycles (vertical box labeled B in FIG. 18A). C. Within superficial layers, current sinks that constitute γ-oscillations propagate at ~200 μm/ms (slope of dotted line). 2-D CSD along superficial layers of the cortical culture for 3 γ-cycles (horizontal box labeled C in FIG. 18A). D. Summary of the CSD profile along the cortical culture depth for γ and θ LFP activity respectively (Average from n=7 cultures plotted for positive (peak) and negative (trough) within one cycle).

At every time point, the CSD was calculated as the negative Laplacian of local field potential (_) on the multi-electrode array as given by $$CSD \sim -\left(\frac{\partial^2 \varphi}{\partial^2 x^2} + \frac{\partial^2 \varphi}{\partial^2 y^2}\right), \qquad (10)$$

which is approximated in the formula $$CSD_{xy} \approx \frac{\varphi_{x+1,y} + \varphi_{x-1,y} + \varphi_{x,y+1} + \varphi_{x,y-1} - 4\varphi_x}{(\Delta z)^2} \qquad (11)$$

where x and y coordinate represent the rows and column positions on the multielectrode array and $\Delta z$ represents the inter-electrode distance which is the same in both x and y directions. This formula allows the calculation of the CSD at all inner electrodes of the multielectrode array. To identify the main source-sink distribution during one oscillation cycle, the CSD profile was first analyzed at the positive peak of the mean oscillatory activity. First, LFPs from all electrodes were averaged for one oscillatory activity burst. Then, the CSD was calculated at the time of the 5 highest LFP peaks within a burst and averaged. This procedure was repeated for a total of 150 bursts from each network and for different networks. The average CSD across layers was obtained using one column of the 2DCSD profile and averaged over all networks. This procedure was repeated for the negative peak of the oscillation resulting in two estimates of the sink-source distribution across layers during one oscillation cycle. The spatio-temporal CSD as obtained by the population averaging at two extremes of an oscillation, was further confirmed by calculating CSD for successive time frames during one oscillation burst. The temporal progress of sink and source variation in the array was analyzed by estimating CSDs in every time frame of a burst period. The sink source variation between different layers and across the layers was visually assessed.

Figure 19:
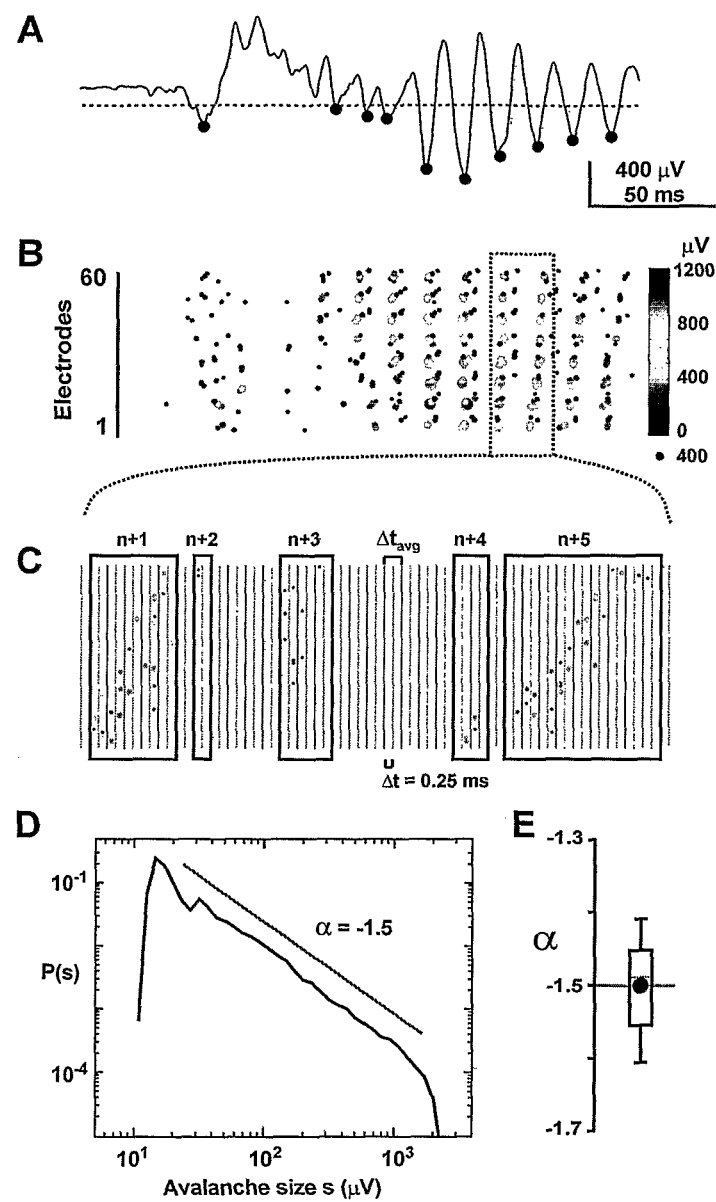
FIGS. 19 A-E illustrate $\gamma$- and $\theta$ oscillations are composed of neuronal avalanches characterized by a power law with slope $\alpha=-1.5$.
Figure 20:
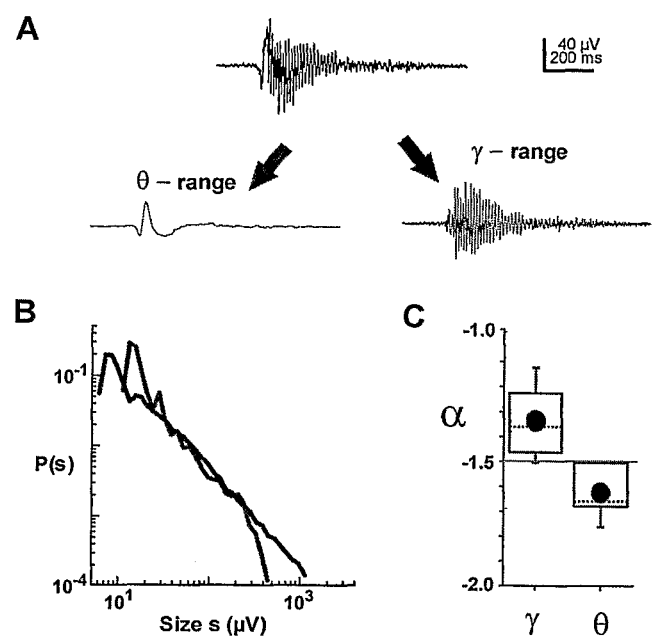
FIGS. 20 A-C illustrate $\gamma$-oscillations reflect periods of high coherence that facilitate large avalanches.

To test the hypothesis, that neuronal avalanches might persist in the presence of oscillatory activity, the signals from all channels were analyzed for LFPs occurring with a peak 3×SD above noise (FIG. 19). This yielded a raster with time of occurrence and peak amplitude of LFPs (FIGS. 19B,C). The data was binned at $\Delta t_{avg}$ obtained from cross correlation analysis. Analysis of the local field potentials, which constituted the oscillations yielded results indicating that even in the presence of the oscillatory activity the network maintains the critical state dynamics. Plotting the probability of occurrence of avalanches of different sizes against avalanches in log-log coordinates of different sizes yielded a curve with slope α=−1.5 (FIGS. 19D,E; mean=−1.53±0.02, n=9).

Evidence is provided that the two dominant oscillations present in the spontaneous network activity, i.e. δ/θ- and γ-frequencies, contribute differently to the maintenance of the critical state, i.e. slope α=−1.5. Temporal filtering was used to separate the two main frequency components in the original signal (FIG. 20A) and each frequency band containing one of the dominant frequencies was reanalyzed for the presence of the critical state. Both filtered signals demonstrated a marked deviation from the critical state regime, i.e. power law slope α=−312. The avalanches formed by the γ-oscillations alone, showed a shallower slope in the avalanche size distribution (FIGS. 20B,C; α=−1.35±0.05, n=6 networks) suggesting that γ-oscillations facilitate the occurrence of large avalanches. On the other hand, the δ/θ-frequency band supported smaller avalanche sizes resulting in a steeper slope in avalanche sizes (FIGS. 20B,C; α=−1.63±0.04, n=6 networks). Slopes between δ/θ- and γ-frequencies were significantly different (p=0.01, n=6).

The fact that γ-oscillations favor larger avalanches suggests that they have a role in extensive spread of neuronal activity thereby facilitating the information transmission across large distances in neuronal networks. At the same time the δ/θ-frequency components compensates for excessive avalanche sizes, thereby maintaining the critical network dynamics.

Experimental evidence is provided that the critical state during development is maintained through a balanced D1/D2-receptor activation. Bath application of the dopamine D1-receptor antagonist SCH23390 (10_M) significantly reduced the power of dominant frequencies between 40-120 Hz by more than 50% (FIG. 21Aa1-a3; p=0.003; n=5), whereas it tended to affect γ-frequency components to a lesser extent (FIG. 21Aa2; p=0.45, n=5). The demonstration that large avalanches are primarily supported in the γ-frequency range, suggested that the decrease in γ-frequency should be paralleled by a steeper power law slope a in the avalanche size distribution, i.e. reduction in large avalanches. Indeed, SCH23390 also significantly decreased the slope to α=−1.60±0.04, significant different from the critical value of α=−3/2 (FIG. 21Aa-4,5; p=0.02, n=5). The dopamine D1-receptor receptor blockade also reduced the peak frequency in the high frequency band, which shifted by 59±1% from its original value p=0.01; cp. FIG. 21Aa2). Conversely, blockade of the dopamine D2-receptor using 10 μM sulpiride (FIG. 21B) doubled the power of γ-activity p=0.02) without a change in frequency (FIG. 21Bb1-3; p=0.02; n=5). (cp. FIG. 21Bb2). As expected, the increase in γ-oscillation activity was paralleled by a more shallow power law slope in the avalanche size distribution, i.e. a significant increase in α to −1.37±0.02.

Figure 21:
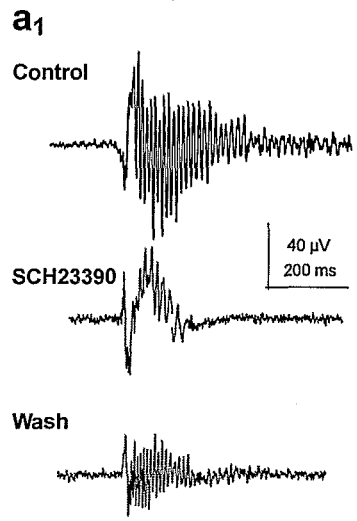
FIGS. 21A-B demonstrate balanced action of dopamine $D_1/D_2$ receptor activation on the formation of neuronal avalanche and $\gamma$-oscillation formation in cortical networks.
Figure 21:
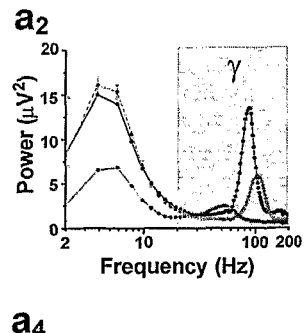
Figure 21:
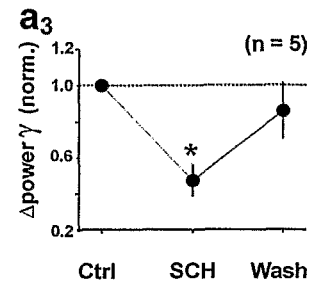
Figure 21:
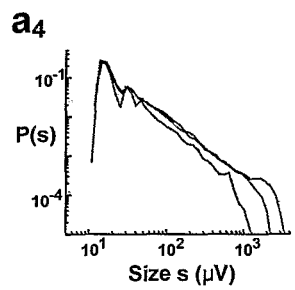
Figure 21:
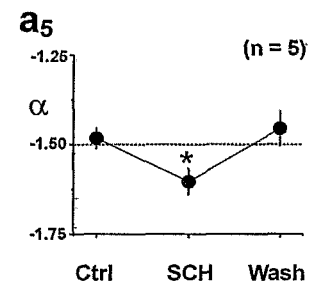
Figure 21:
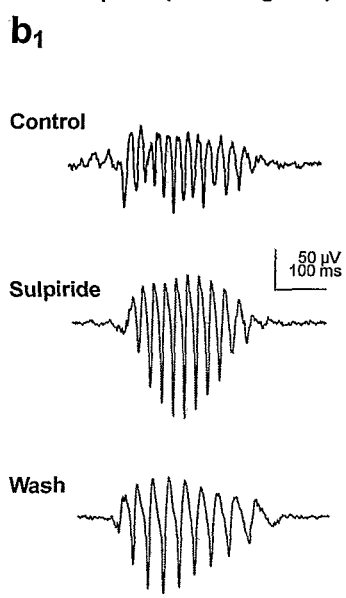
Figure 21:
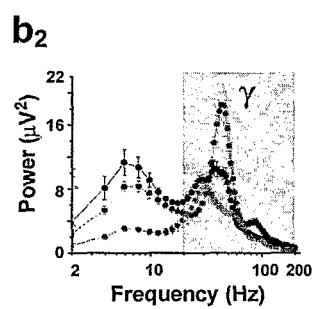
Figure 21:
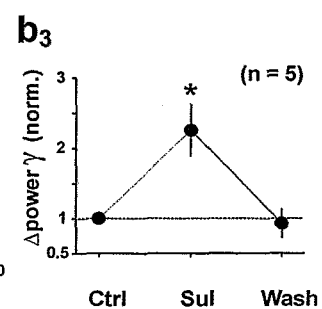
Figure 21:
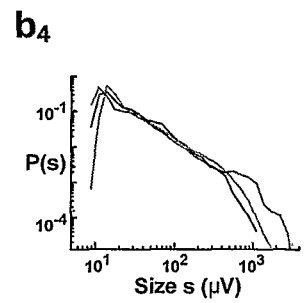
Figure 21:
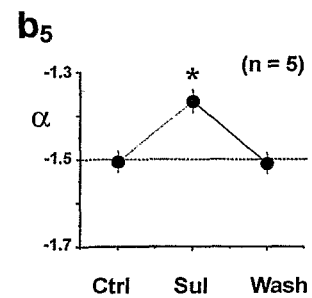

FIG. 21 demonstrates balanced action of dopamine $D_1/D_2$ receptor activation on the formation of neuronal avalanche and γ-oscillation formation in cortical networks. A. Blockade of the dopamine $D_1$ receptor reduces g-oscillations and the power law slope α. (a1) Example bursts before (control), during drug application (10 μM SCH23390), and after (wash). (a2) SCH23390 reduces the power in the frequency spectrum (gray area; single culture). (a3) Summary for the relative drop in frequency power for all 5 cultures (*p<0.005). (a4) SCH23390 results in a steeper power law slope in avalanche size distribution (a5) Summary for the decrease in α for all 5 cultures (*p<0.005). B. Blockade of the dopamine $D_2$ receptor increases oscillations and the power law slope α. (b1) Example bursts before (control), during drug application (10 μM Sulpiride), and after (wash). (b2) Sulpiride increases the power in the frequency spectrum (gray area; single culture). (b3) Summary for the relative increase in γ-frequency power for all 5 cultures (*p<0.005). (b4) Sulpiride results in an increase of the power law slope in avalanche size distribution. (b5) Summary in increase in α for all 5 cultures (*p<0.005).

The dopamine $D_1$ receptor antagonist R(+)-7-Chloro-8-hydroxy-3-methyl-1-phenyl-2,3,4,5-tetrahydro-1H-3-benzazepine hydrochloride (SCH23390; Sigma-Aldrich) was first dissolved in Artificial Cerebrospinal Fluid (ACSF) at a concentration of 2 mM. About 3 μl of the stock solution was added to the ~600 μl of culture media in the multielectrode array chamber to reach a final concentration of 10 μM. Similarly, the dopamine $D_2$ receptor antagonist sulpiride (RBI) was first dissolved in DMSO and then added to the multielectrode array chamber to reach a final concentration of 10 μM. The concentration of DMSO in the working solution was limited to 0.01%. Each addition of the drug was followed by 4 hours of continuous recording, after which the culture was washed by replacing the culture medium with 50% of conditioned media (collected from the same culture the day before drug application) and 50% of fresh, unconditioned medium, followed by 4-8 hrs of recording.

Figure 22:
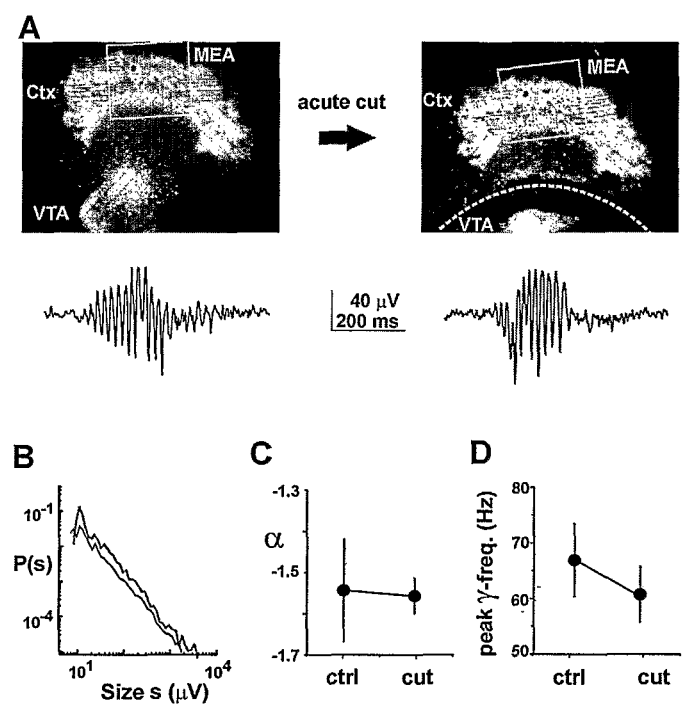
FIGS. 22 A-D demonstrate that $\gamma$-oscillations originate within cortical superficial layers and do not depend on acute inputs from the VTA.

These findings demonstrate that the dopamine $D_1$ and $D_2$ receptor activation has opposing effects on the formation of neuronal avalanche and γ-oscillations. The balanced activation of both receptors stabilizes the cortical network in the critical state, characterized by a power law slope $\alpha=-3/2$. This is a means by which the system can maintain critical dynamics while retaining its capacity for generating larger avalanches with extensive spatiotemporal spread Experimental evidence is provided that the oscillatory activity in cortical networks in the critical state does dependent on direct neuronal inputs from VTA. Neuronal connections between the cortex and VTA culture were cut using a micro scalpel (FIG. 22). Under visual control using a stereoscope, a microrazor blade was placed perpendicular to the surface of the multielectrode array along the border between cortex and VTA and slight pressure was applied. This resulted in a clear opening of the plasma-thrombin coat exposing the multielectrode array surface along a gap of several millimeter length and ~1 mm width. Visual inspection of this gap devoid of any neuronal tissue; tissue bridges between the cultures and the clear exposure of the multielectrode array surface was used as a control to ensure mechanical VTA separation from the cortical culture. The electrical activity in the cortical region was recorded immediately prior and after separation of the two tissue areas. In order to address whether direct synaptic inputs from VTA are responsible for spontaneous γ-oscillation bursts, cortical activity was recorded before and immediately after removal of VTA inputs in the co-culture. The acute lesion did not affect γ oscillations or critical dynamics in the network (FIG. 22) demonstrating that the fast γ-oscillation activity originated within cortical superficial layers.

FIG. 22 demonstrates that γ-oscillations originate within cortical superficial layers and do not depend on acute inputs from the VTA. A. Cortex-VTA co-culture before (left) and after an acute lesion of VTA inputs (right; broken yellow line). Square: MEA position; Filled dot: Cortical recording location of spontaneous single LFP burst before (bottom left) and after (bottom right) the acute lesion. B. Neuronal avalanche size distributions are not affected by the acute removal of VTA inputs (single network). C. The avalanche size slope $\alpha=-1.5$ is preserved after the acute lesion, so is the average peak frequency of the g-oscillation (D). (n=3 experiments).

Figure 23:
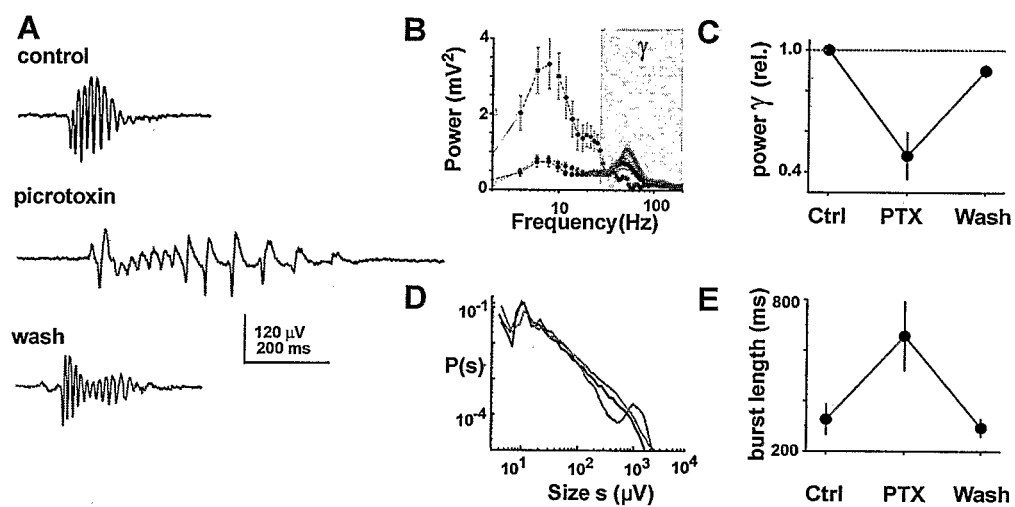
FIGS. 23 A-E demonstrate that γ-oscillations composed of neuronal avalanches during early development depend on intact fast GABAA-mediated synaptic inhibition.

Avalanches based on non-oscillatory extracellular activity reveal a slope in size distribution steeper than −3/2 when inhibition is reduced. In line with these findings, avalanches formed during δ/θ- and γ-oscillations also change their slope when $GABA_A$-mediated synaptic inhibition is reduced (FIG. 23). Bath-application of 5 μM picrotoxin greatly reduced γ-oscillations by more than 50% (FIGS. 23A,B) and periods of activity changed from a sinusoidal-like oscillation to a sequential activation of isolated, ictal spikes, typical for epileptic activity (FIG. 23A). Inhibition of GABAA inputs can reduce the frequency of oscillatory activity in the γ-range. Avalanche sizes distribution in the presence of picrotoxin were almost bimodal (FIG. 23D) distribution as described previously for mature slices and mature cortical cultures.

FIG. 23 demonstrates that γ-oscillations composed of neuronal avalanches during early development depend on intact fast $GABA_A$-mediated synaptic inhibition. A. Example bursts before (control, during drug application (lI0 μM picrotoxin; PTX), and after (wash). B. PTX significantly decreases the power in the γ-frequency spectrum (gray area; single culture) and increases the power in the δ/θ-frequency range. C. Summary for the relative decrease in γ-frequency power for all 5 cultures (*p<0.005; n=3 cultures). D. PTX changes the avalanche size distribution as reported previously for adult mature cultures and slices. E. PTX increases the average burst duration in the network (*p<0.05; n=3 cultures).

D. Example 4

Anti-Epileptic Measures Using Avalanche Size Distributions

The NAS assay can be used to study the anti-epileptic property of a drug. In epileptic discharge, the balance of excitation and inhibition is disturbed. In order to demonstrate that the NAS-assay can be used to study anti-epileptic propensities of compositions, experimental evidence is provided that a perturbation of either excitatory transmission or inhibitory transmission moves the tissue out of the critical state.

Provided is a precise quantitative framework to determine the perturbance in excitatory or inhibitory balance.

Organotypic cortex cultures from rat were grown for 3-4 weeks on an 8×8 microelectrode array in a custom-designed incubator as described above. Spontaneous activity in the form of local field potentials was recorded for up to 5 hrs and processed for neuronal avalanches (n=6). Under normal conditions, avalanche sizes sLFP were distributed according to a power law with a slope $\alpha=-1.5$, which demonstrates that these networks were in the 'critical' state as reported previously (FIG. 24A).

A reduction in excitatory synaptic transmission in the critical state is expected to increase propagation failure thus reducing avalanche sizes. While an overall decrease in avalanche sizes would shift the size distribution to the left with no change in $\alpha$, a decrease in large avalanches solely would change the cut-off of the distribution, again with no change in $\alpha$. Alternatively, a reduction in excitation could affect avalanches of varying sizes differently thereby changing the slope $\alpha$. Indeed, when the glutamate AMPA receptor antagonist DNQX (3 μM) was bath-applied to cultured networks in the critical state, the power law in avalanche size was largely preserved, however, its slope $\alpha$ decreased close to −2, which was significantly smaller than −1.5 (Table 1; P<0.05). Thus, when the network is less excitable, larger avalanches are increasingly less likely to emerge (FIG. 24B).

According to the previous results, if a network in the critical state is made slightly more excitable, by e.g. a modest reduction in fast GABAergic synaptic inhibition, activity should spread more efficiently thus increasing the likelihood for larger avalanche sizes. Again, this could have various effects on the avalanche size distribution including a change in a to a value greater than −1.5. Bath-application of a relatively low dose of the $GABA_A$-antagonist picrotoxin (2-3 μM), however, did not further increase the slope (, but instead changed the power law to a bimodal distribution with an initial slope $\alpha=-1.8$, which again was smaller than −1.5 in accordance with previous findings (FIG. 24C). The bimodal size distribution indicates the presence of a size threshold in the system that is avalanches tend to be either small and local or very large and engage the whole network (FIG. 24C, arrow), a feature of epileptic activity, which is in line with the finding that blocking fast $GABA_A$ synaptic transmission induces strong epileptic activity in cortical networks. The preference for large avalanches is easily quantified as the likelihood of observing large avalanches beyond what is predicted from the linear regression analysis ($\Delta P_{max}$, FIGS. 24B, C).

It is sometimes more convenient to express avalanches sizes in number of electrode ($s_{ele}$), particularly when the detection of an LFP is not a problem, but when the derivation of its exact amplitude is difficult because of non-linear microelectrode characteristics and/or non-optimal placement of electrodes within the neuronal tissue. For example, planar microelectrode recordings in acute slices are highly distorted in amplitude due to the relatively large distance between active sites in the slice and the surface placement of the electrodes. Results did not differ when avalanche size distributions were based on $s_{LFP}$, or $s_{ele}$ (FIG. 24).

Figure 24:
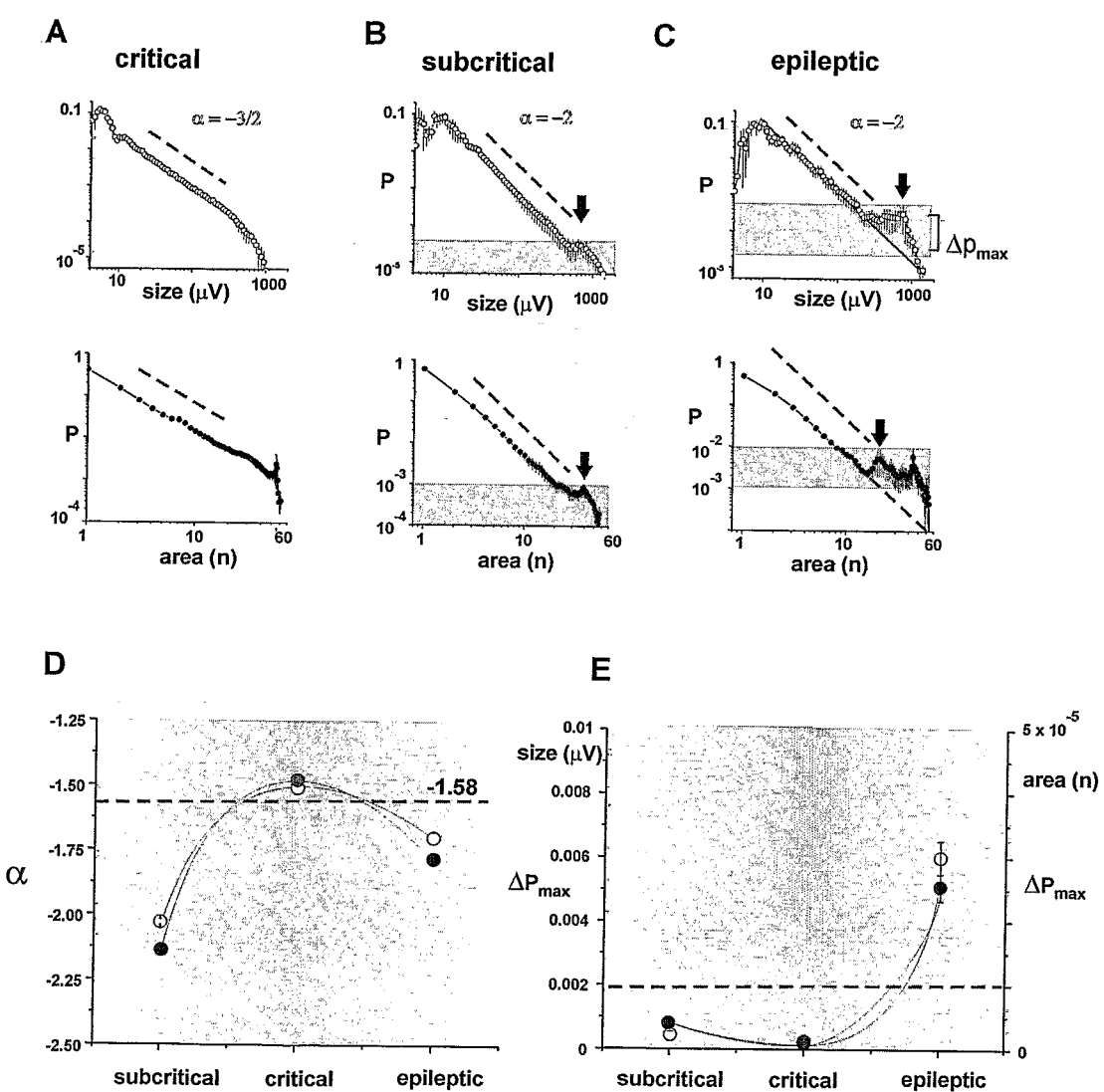
FIGS. 24 A-E illustrate the slope and shape of avalanche size distributions provide a precise and quantitative measure for the sub-critical, critical, and epileptic state in cortical networks.

FIG. 24 illustrates the slope and shape of avalanche size distributions provide a precise and quantitative measure for the sub-critical, critical, and epileptic state in cortical networks. A. In the critical state, a slope $\alpha=-1.5$ characterizes the power law in avalanche size distribution $s_{LFP}$ (left) and $s_{ele}$ (right) (broken line; mean±s.e.m; 6 cortical cultures). B. In the subcritical state, in which fast excitatory transmission is slightly reduced by the AMPA glutamate receptor antagonist DNQX (3 μM), the power law in avalanche size distribution changes to a slope $\alpha \sim -2$ (broken line; mean±s.e.m; 6 cortical cultures). C. In the epileptic state, in which fast inhibition is slightly reduced with the $GABA_A$-antagonist picrotoxin (3 μM), the avalanche size distribution becomes bimodal with an initial slope $\alpha \sim -2$ (broken line). Note that the over-representation of large avalanches (arrow) is about ~10 times higher in the epileptic state compared to the sub-critical state for $s_{LFP}$ (left) as well as $s_{ele}$ (right; gray regimes). Left: $s_{LFP}$. right: $s_{ele}$. Summary of state identification for sub-critical, critical, and epileptic states. D. A slope in $\alpha=-1.5$ indicates the critical state and is the largest slope that can be obtained in cortical avalanche dynamics. E. A large positive deviation for large avalanches from the power law indicates epileptic activity, while a small positive deviation indicates the sub-critical and critical state respectively.

Taken together, the two parameters $\alpha$ and $\Delta P_{max}$ allow for an easy and robust classifications of the critical, sub-critical, and epileptic state in cortical networks. First, a maximal slope value of $\alpha=-1.5$ separates the critical regime from non-critical regimes (FIG. 24D). Second, a large value for $\Delta P_{max}$ separates the sub-critical and critical regime from the epileptic regime (FIG. 24E).

E. Example 5

A Drug's Epileptogenic Potential

The NAS assay can be used to study the epileptogenic potential of a drug or composition. The atypical neuroleptic clozapine preferentially releases dopamine in the medial prefrontal cortex (mPFC) of rat and rhesus monkey, shows agonist action at the NMDA receptor, and at the single neuron level, enhances NMDA currents. The drug can be considered a candidate to elicit neuronal avalanches in prefrontal cortex slices through dopamine-NMDA interaction.

The NAS-assay demonstrates that the atypical neuroleptic clozapine at a concentration of 100 nM, which is within the therapeutically advised regime and slightly lower than maximal receptor occupancy in humans, induces neuronal avalanches in prefrontal cortex slices, but the resulting dynamics is epileptic. Thus, the in vitro NAS screen successfully captures two main feature of clozapine action in vivo: the drug's potential to affect prefrontal cortex activity and its epileptogenic potential in schizophrenic patients.

Clozapine, when bath-applied at 100 nM, was highly effective in inducing neuronal avalanches in acute slices from rat medial prefrontal cortex. Within minutes, LFP activity in the form of negative population spikes occurred for a total duration of ~40 min (FIGS. 25A,B). As reported for avalanches induced by dopamine and NMDA (see above), clozapine induced LFP activity in superficial cortical layers only (FIG. 25C). Furthermore, when LFPs were processed for neuronal avalanches at $\Delta t_{avg}=1$ ms, the corresponding avalanche size distribution for $s_{LFP}$ was characterized by an initial slope $\alpha_{LFP}=-2.00\pm0.13$, which was not critical (R=0.965; n=49; range 5-60 μV). Similarly, the distribution of avalanche size $s_{ele}$ based on electrode count revealed a slope $\alpha_{ele}=-2.07\pm0.08$, which also was not critical. Furthermore, the size distributions clearly revealed a positive value of $\Delta P_{max}=0.006$, which identified the neuronal avalanche dynamics induced by clozapine as epileptic (FIG. 4D), in line with the high epileptogenic potential of clozapine in human studies.

Figure 25:
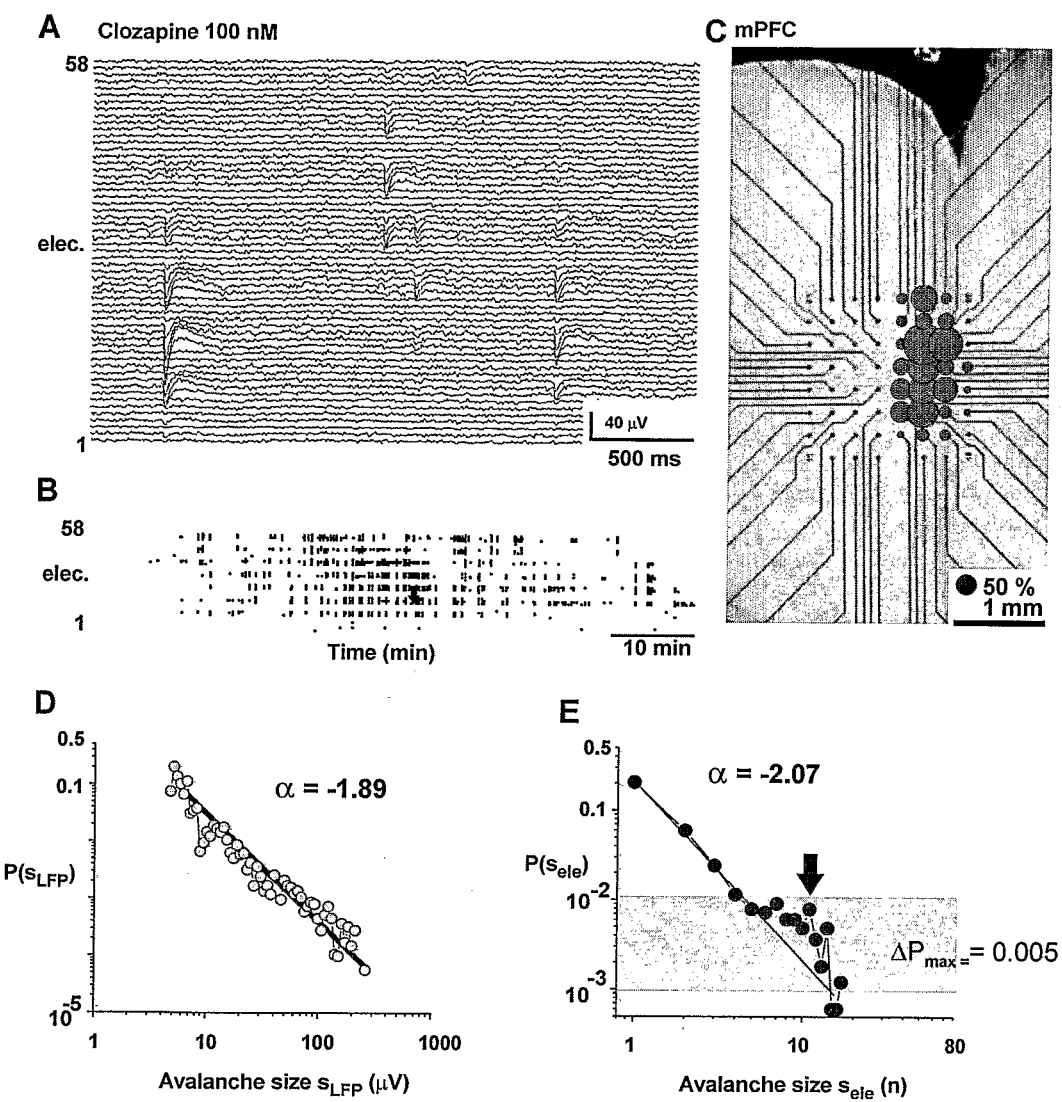
FIGS. 25 A-E illustrate the atypical neuroleptic clozapine induces epileptic, neuronal avalanche activity in acute slices of adult rat mPFC.

FIG. 25 illustrates the atypical neuroleptic clozapine induces epileptic, neuronal avalanche activity in acute slices of adult rat mPFC. A, Bath-application of 100 nM clozapine gives rise to spontaneous LFP activity characterized by the irregular occurrence of negative population spikes clustered across electrodes (Drug was applied at t=0 and was present throughout the experiment. B, Full raster display of LFP activity on the multi-electrode array (linear order of electrodes). Each dot represents the time of a negative LFP peak. C, Corresponding light-microscopic image of the acute coronal slice showing the position of the 8×8 electrode array on the mPFC and the normalized LFP density per electrode (dot diameter). D, E, An initial slope $\alpha$ much steeper than −1.5 characterizes the distribution in avalanche sizes $S_{LFP}$ and $s_{ele}$ in mPFC slices induced by clozapine. A clear bimodal shape with a preference of larger avalanches (arrow) demonstrates the epileptic character of the activity induced by clozapine.

F. Example 6

The Effect of Anti-Muscarinergic Agents on the Critical State

Cholinergic function has been shown to be important for cognitive cortical processing. Disturbances of the cholinergic system can have serious cognitive deficits as seen in e.g. Alzheimer's disease. The Neuronal avalanche size (NAS)-assay allows for the measurement of how cholinergic drugs optimize network function (see below) and will be particularly useful to screen for non-epileptogenic, cognitive enhancers in Alzheimer's disease.

Previous experiments demonstrated in rat medial prefrontal cortex that bath-application of 3 μM NMDA and 3 μM of the dopamine D1-receptor agonist SKF38393 induces neuronal avalanches with an optimal power law slope of −1.5 in the avalanche size distribution. Here experimental evidence is provided, which shows that this optimal network performance is not achieved when, in addition, muscarinergic receptors are blocked in the cortex, using the broadband muscarinergic antagonist atropine (10 μM; n=6). While atropine did not block neuronal avalanche induction (FIG. 26), it reduced the power law slope to $\alpha_{LFP}=-1.696\pm0.045$, which was significantly from control ($\alpha_{LFP}=-1.499\pm0.005$; 3 μM NMDA and 3 μM SKF38393; n=11; t=−8.4224, v=108, p<0.005).

Figure 26:
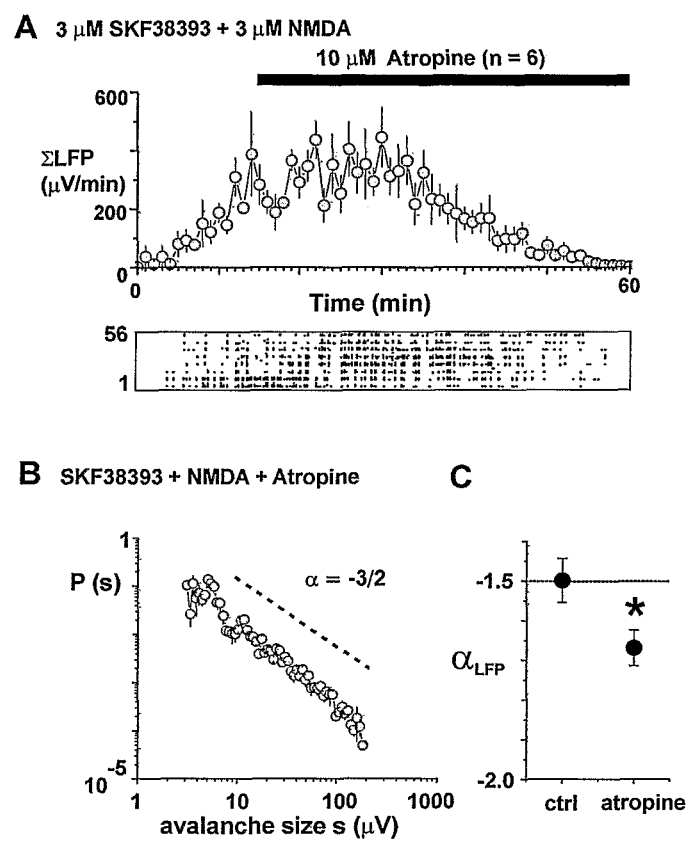
FIGS. 26 A-C illustrate-avalanche induction is sub-optimal when muscarinergic receptors are blocked in mPFC of aged rats (>2 months).

FIG. 26 illustrates avalanche induction is sub-optimal when muscarinergic receptors are blocked in mPFC of aged rats (>2 months). A, Blockade of muscarinergic receptors with atropine (10 μM) does not prevent avalanche activity. B, Corresponding power law in avalanche event size distribution for the experiments shown in A. C, The power law slope is significantly different from the optimal value of −1.5 when muscarinergic receptors are blocked ($P<0.005$).

While this invention has been described in connection with preferred embodiments and specific examples, it is not intended that the scope of the invention be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining a cognitive enhancement effect comprising:
    administering or applying to a human subject a composition suspected of having a cognitive enhancement and/or anti-epileptic effect to neuronal tissue;
    detecting synchronized neuronal activity in neuronal tissue;
    monitoring spreading of the synchronized neuronal activity;
    determining a parameter indicative of the closeness of the synchronized neuronal activity to a critical state; and
    comparing the parameter to a predetermined value, thereby determining the cognitive enhancement, wherein the parameter is a slope of a size distribution of the synchronized neuronal activity and the predetermined value is −3/2.

2. The method of claim 1, wherein the parameter is a ratio of successively propagated synchronized neuronal activity and the predetermined value is 1.

3. The method of claim 2 wherein if the ratio is equal to 1, the effect is optimal, and if the ratio is smaller or larger than 1, the effect is sub-optimal.

4. The method of claim 1, wherein detecting synchronized neuronal activity is selected from the group consisting of:
    microelectrode array;
    magnetoencephalograph;
    electroencephalograph;
    magnetic resonance imaging; and
    imaging with fluorescent probes.

5. The method of claim 1, wherein the synchronized neuronal activity is selected from the group consisting of:
    local field potentials;
    magnetic currents;
    single or multi-unit activity; and
    fluorescent probes.

6. The method of claim 1 wherein the cognitive enhancement effect is selected from the group consisting of:
    dopaminergic;
    glutamatergic;
    GABAergic;
    cholinergic;
    serotonergic; and
    noradrenergic.

7. The method of claim 1 wherein if the slope is equal to the −3/2, the effect is optimal, and if the determined slope is steeper than −3/2, the effect is sub-optimal.

8. A method for determining a cognitive enhancement effect comprising:
    administering or applying to a human subject a composition suspected of having a cognitive enhancement to neuronal tissue;
    detecting synchronized neuronal activity in neuronal tissue;
    monitoring spreading of the synchronized neuronal activity;
    determining a slope of a size distribution of the synchronized neuronal activity;
    comparing the slope of the size distribution to a threshold slope;
    determining a branching ratio of successively propagated synchronized neuronal activity; and
    comparing the branching ratio to a threshold ratio, thereby determining the cognitive enhancement, wherein the threshold slope is −3/2 and the threshold branching ratio is 1 or $\log(1)=0$.

9. The method of claim 8, wherein detecting synchronized neuronal activity is selected from the group consisting of:
    microelectrode array;
    magnetoericephalograph;
    electroencephalograph;
    magnetic resonance imaging; and
    imaging with fluorescent probes.

10. The method of claim 8, wherein the synchronized neuronal activity is selected from the group consisting of:
    local field potentials;
    magnetic currents;
    single or multi-unit activity; and
    fluorescent probes.

11. The method of claim 8 wherein the cognitive enhancement effect is selected from the group consisting of:
    dopaminergic;
    glutamatergic;
    GABAergic;
    cholinergic;
    serotonergic; and
    noradrenergic.

12. The method of claim 8 wherein (i) if the determined slope is equal to the threshold slope, the effect is optimal, and (ii) if the determined slope is steeper than the threshold slope, the effect is sub-optimal.

13. The method of claim 8 wherein (i) the determined branching ratio is equal to 1, the effect is optimal, and (ii) if the determined branching ratio is smaller or larger than 1, the effect is sub-optimal.

14. The method of claim 8 wherein if the determined branching ratio is smaller or larger than 1, the effect is sub-optimal.

15. A method for determining an anti-epileptic effect in a human subject comprising:
  administering or applying to the human subject a composition suspected of having an anti-epileptic effect to human neuronal tissue;
  detecting synchronized neuronal activity in neuronal tissue;
  monitoring spreading of the synchronized neuronal activity;
  determining a parameter indicative of the closeness of the synchronized neuronal activity to a critical state; and
  comparing the parameter to a predetermined value, wherein the parameter is a slope of a size distribution of the synchronized neuronal activity and the predetermined value is −3/2, thereby determining the anti-epileptic effect.

16. The method of claim 15, wherein the parameter is a ratio of successively propagated synchronized neuronal activity and the predetermined value is 1.

17. The method of claim 16 wherein (i) if the ratio is equal to 1, the effect is optimal, and (ii) if the ratio is smaller or larger than 1, the effect is sub-optimal.

18. The method of claim 15, wherein detecting synchronized neuronal activity is selected from the group consisting of:
  microelectrode array;
  magnetoencephalograph;
  electroencephalograph;
  magnetic resonance imaging; and
  imaging with fluorescent probes.

19. The method of claim 18 wherein the anti-epileptic effect is selected from the group consisting of:
  dopaminergic;
  glutamatergic;
  GABAergic;
  cholinergic;
  serotonergic; and
  noradrenergic.

20. The method of claim 15 wherein the synchronized neuronal activity is selected from the group consisting of:
  local field potentials;
  magnetic currents;
  single or multi-unit activity; and
  fluorescent probes.

21. The method of claim 15 wherein (i) if the slope is equal to the −3/2, the effect is optimal, and (ii) if the determined slope is steeper than −3/2, the effect is sub-optimal.

22. A method for determining an anti-epileptic effect in a human subject comprising:
  administering or applying to a human subject a composition suspected of having an anti-epileptic effect to human neuronal tissue;
  detecting synchronized neuronal activity in neuronal tissue;
  monitoring spreading of the synchronized neuronal activity;
  determining a slope of a size distribution of the synchronized neuronal activity;
  comparing the slope of the size distribution to a threshold slope;
  determining a branching ratio of successively propagated synchronized neuronal activity; and
  comparing the branching ratio to a threshold ratio, wherein the threshold slope is −3/2 and the threshold branching ratio is 1 or log(1)=0, thereby determining the anti-epileptic effect.

23. The method of claim 22 wherein detecting synchronized neuronal activity is selected from the group consisting of:
  microelectrode array;
  magnetoencephalograph;
  electroencephalograph;
  magnetic resonance imaging; and
  imaging with fluorescent probes.

24. The method of claim 22 wherein the synchronized neuronal activity is selected from the group consisting of:
  local field potentials;
  magnetic currents;
  single or multi-unit activity; and
  fluorescent probes.

25. The method of claim 24 wherein (i) if the determined branching ratio is equal to 1, the effect is optimal, and (ii) if the determined branching ratio is smaller or larger than 1, the effect is sub-optimal.

26. The method of claim 22 wherein the anti-epileptic effect is selected from the group consisting of:
  dopaminergic;
  glutamatergic;
  GABAergic;
  cholinergic;
  serotonergic; and
  noradrenergic.

27. The method of claim 22 wherein (i) if the determined slope is equal to the threshold slope, the effect is optimal, and (ii) if the determined slope is steeper than the threshold slope, the effect is sub-optimal.

* * * * *